United States Patent [19]

Sunagawa et al.

[11] Patent Number: 5,227,376
[45] Date of Patent: Jul. 13, 1993

[54] β-LACTAM COMPOUNDS AND THEIR PRODUCTION

[75] Inventors: Makoto Sunagawa; Akira Sasaki, both of Hyogo; Hiroshi Yamaga, Osaka; Masatomo Fukasawa, Hyogo; Hiroshi Nouda, Osaka, all of Japan

[73] Assignee: Sumitomo Pharmaceuticals Co., Ltd., Osaka, Japan

[21] Appl. No.: 928,170

[22] Filed: Aug. 14, 1992

Related U.S. Application Data

[63] Continuation of Ser. No. 653,954, Feb. 12, 1991, abandoned.

[30] Foreign Application Priority Data

Feb. 14, 1990 [JP] Japan .................................. 2-34952

[51] Int. Cl.⁵ .................... A01N 43/00; C07D 487/04
[52] U.S. Cl. ..................................... 514/210; 540/350
[58] Field of Search ......................... 540/350; 514/210

[56] References Cited

FOREIGN PATENT DOCUMENTS

| | | |
|---|---|---|
| 0126587 | 11/1984 | European Pat. Off. . |
| 0168707 | 1/1986 | European Pat. Off. . |
| 0170073 | 2/1986 | European Pat. Off. . |
| 0182213 | 5/1986 | European Pat. Off. . |
| 0235823 | 9/1987 | European Pat. Off. . |
| 0242134 | 10/1987 | European Pat. Off. . |
| 0243686 | 11/1987 | European Pat. Off. . |
| 0289801 | 11/1988 | European Pat. Off. . |
| 0333175 | 9/1989 | European Pat. Off. . |
| 0337637 | 10/1989 | European Pat. Off. . |
| 0343499 | 11/1989 | European Pat. Off. . |
| 0358085 | 3/1990 | European Pat. Off. . |

OTHER PUBLICATIONS

Chemical Abstracts 110:75160a.
Kim et al., J. Med. Chem. 32, 602–604 (1989).
Deziel, Tetrahedron Letters, vol. 28, No. 38, 4371–4372 (1987).

*Primary Examiner*—Marianne M. Cintins
*Assistant Examiner*—Rebecca Cook
*Attorney, Agent, or Firm*—Birch, Stewart, Kolasch & Birch

[57] ABSTRACT

A compound of the formula:

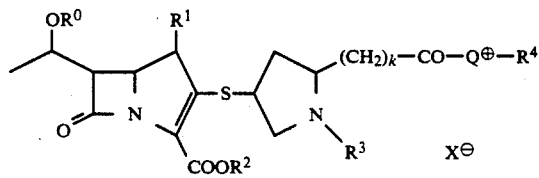

, which is useful as an antimicrobial agent.

11 Claims, No Drawings

β-LACTAM COMPOUNDS AND THEIR PRODUCTION

This application is a continuation of application Ser. No. 07/653,954 filed on Feb. 12, 1991, now abandoned.

The present invention relates to β-lactam compounds and their production. More particularly, it relates to novel 3-pyrrolidinylthio-1-azabicyclo[3.2.0]-hept-2-en-7-one-2-carboxylic acid compounds bearing a quaternary ammonium group on the pyrrolidine ring and their production.

There are known some β-lactam compounds having a carbapenem skeleton, which possess an excellent antimicrobial spectrum against a wide range of Gram-positive and Gram-negative bacteria. Among them, imipenem is already available on the market. Since, however, imipenem is sensitive to renal dehydropeptidase-I (DHP-I) in a living body and apt to be inactivated, it is normally used in combination with cylastatin for preventing the inactivation with DHP-I. Needless to say, it is clinically favorable that an antimicrobial agent exerts its antimicrobial activity without any auxiliary agent, and a great demand is present towards the development of a β-lactam compound which exerts its antimicrobial activity with resistance to DHP-I, i.e. saving the use of any auxiliary agent.

As the result of an extensive study, it has now been found that some 3-pyrrolidinylthio-1-azabicyclo[3.2.0]-hept-2-en-7-one-2-carboxylic acid compounds having a quaternary ammonium group on the pyrrolidine ring exerts a strong antimicrobial activity with sufficient resistance to DHP-I. The present invention is based on the above finding.

Accordingly, a basic object of the present invention is to provide a novel β-lactam compound of the formula:

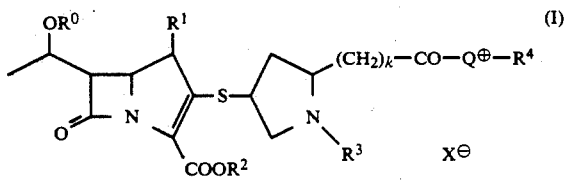

wherein $R^0$ is a hydrogen atom or a protective group for hydroxyl, $R^1$ is a lower alkyl group, $R^2$ is a protective group for carboxyl or a negative charge, $R^3$ is a hydrogen atom or a protective group for amino, $R^4$ is a lower alkyl group or a substituted lower alkyl group, k is an integer of 0 to 4, X is an acid residue or intramolecular COO when $R^2$ is the negative charge and $Q^\oplus$ is a quaternary nitrogen atom-containing group represented by either one of the formulas (1) to (4):

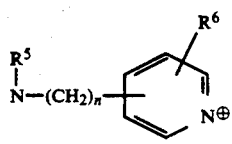

wherein $R^5$ is a hydrogen atom, a lower alkyl group or a 2-hydroxyethyl group, $R^6$ is a hydrogen atom or a lower alkyl group and n is an integer of 0 to 4;

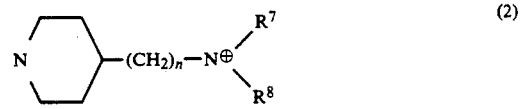

wherein $R^7$ and $R^8$ are each a lower alkyl group or may be combined together to form a lower alkylene group, or $R^8$ represents a substituted lower alkyl group and n is as defined above;

wherein $R^9$ is a lower alkyl group or a substituted lower alkyl group; or

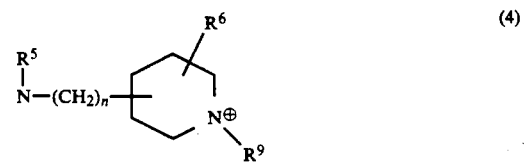

wherein $R^5$, $R^6$, $R^9$ and n are each as defined above.

When $R^2$ is a negative charge and X is intramolecular COO, the β-lactam compound (I) forms an intramolecular quaternary salt, which is represented by the formula:

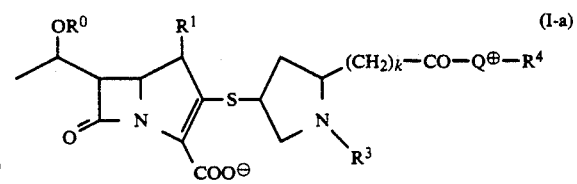

wherein $R^0$, $R^1$, $R^3$, $R^4$, k and $Q^\oplus$ are each as defined above.

Among various β-lactam compounds which fall within the formula (I), the most preferred are those of the formula:

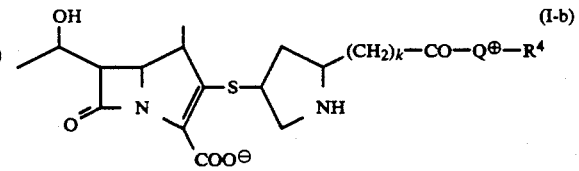

wherein $R^4$, k and $Q^\oplus$ and are each as defined above.

According to the present invention, the β-lactam compound (I) can be produced by reacting a β-lactam compound of the formula:

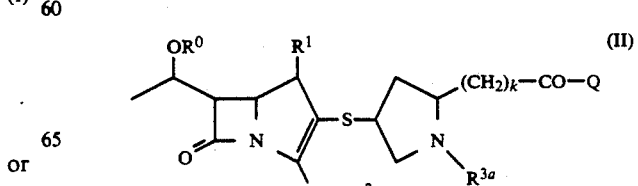

wherein $R^0$, $R^1$ and k are each as defined above, $R^{2a}$ is a protective group for carboxyl, $R^{3a}$ is a protective group for amino and Q is a tertiary nitrogen atom-containing group resulting from elimination of a positive charge from either one of the groups (1) to (4) represented by $Q^\oplus$ with a compound of the formula:

wherein $R^4$ is as defined above and $X^a$ is an acid residue to give a β-lactam compound of the formula:

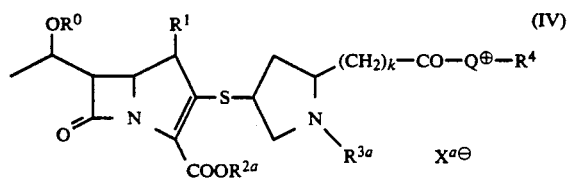

wherein $R^0$, $R^1$, $R^{2a}$, $R^{3a}$, $R^4$, k, $Q^\oplus$ and $X^a$ are each as defined above, optionally followed by subjecting the β-lactam compound (IV) to elimination of the hydroxyl-protecting group represented by $R^0$, elimination of the carboxyl-protecting group represented by $R^{2a}$ and/or elimination of the amino-protecting group represented by $R^{3a}$, thereby giving the δ-lactam compound (I) wherein $R^0$ and $R^3$ are each a hydrogen atom and $R^2$ is a negative charge.

With respect to the definitions of the symbols as given above, the term "lower" is intended to mean a group normally having not more than 8 carbon atoms, preferably not more than 5 carbon atoms.

The protective group for hydroxyl (i.e. hydroxyl-protecting group) represented by $R^0$ and the protective group for amino (i.e. amino-protecting group) represented by $R^3$ or $R^{3a}$ may be any group as conventionally used in the related art field. Preferred examples are $C_1-C_5$ alkoxycarbonyl (e.g. t-butyloxycarbonyl), halo($C_1-C_5$)alkoxycarbonyl (e.g. 2-iodoethyloxycarbonyl, 2,2,2-trichloroethyloxycarbonyl), $C_3-C_7$ alkenyloxycarbonyl (e.g. allyloxycarbonyl), ar-($C_1-C_3$)alkyloxycarbonyl such as phenyl($C_1-C_3$)alkyloxycarbonyl (e.g. benzyloxycarbonyl) or substituted phenyl-($C_1-C_3$)alkyloxycarbonyl (e.g. p-methoxybenzyloxycarbonyl, o-nitrobenzyloxycarbonyl, p-nitrobenzyloxycarbonyl), tri-($C_1-C_5$)alkylsilyl (e.g. trimethylsilyl, t-butyldimethylsilyl), etc.

The protective group for carboxyl (i.e. carboxyl-protective group) represented by $R^2$ or $R^{2a}$ may be also any group as conventionally used. Preferred examples are straight or branched $C_1-C_5$ lower alkyl (e.g. methyl, ethyl, isopropyl, t-butyl), halo($C_1-C_5$)alkyl (e.g. 2-iodoethyl, 2,2,2-trichloroethyl), $C_1-C_5$ alkoxymethyl (e.g. methoxyethyl, ethoxymethyl, isobutoxymethyl), $C_1-C_5$ aliphatic acyloxymethyl (e.g. acetoxymethyl, propionyloxymethyl, butyryloxymethyl, pivaloyloxymethyl), 1-($C_1-C_5$)alkoxycarbonyloxyethyl (e.g. 1-ethoxycarbonyloxyethyl), ar-($C_1-C_3$)alkyl such as phenyl($C_1-C_3$)alkyl (e.g. benzyl) or substituted phenyl(-$C_1-C_3$)alkyl (e.g. p-methoxybenzyl, o-nitrogenzyl, p-nitrobenzyl), $C_3-C_7$ alkenyl (e.g. allyl, 2-methylallyl, 3-methylallyl), benzhydryl, phthalidyl, etc.

Examples of the lower alkyl group represented by $R^1$, $R^4$, $R^5$, $R^6$, $R^7$, $R^8$ or $R^9$ are $C_1-C_5$ alkyl (e.g. methyl, ethyl, n-propyl, isopropyl, n-butyl, n-pentyl), etc. In case of the substituted lower alkyl group represented by $R^4$, $R^8$ or $R^9$, the substituent on the lower alkyl group may be, for instance, carboxyl, lower alkanoyl (e.g. acetyl, propionyl), carbamoyl, lower alkylaminocarbonyl (e.g. methylaminocarbonyl), di(lower)alkylaminocarbonyl (e.g. dimethylaminocarbonyl), cyano, lower alkoxy (e.g. methoxy, ethoxy), hydroxyl, phenyl, etc. Thus, examples of the substituted lower alkyl group are $C_1-C_7$ alkyl substituted with one or more substitutents as exemplified above, specifically carboxymethyl, acetylmethyl, propionylmethyl, carbamoylmethyl, N-methylaminocarbonylmethyl, N,N-dimethylaminocarbonylmethyl, 2-cyanoethyl, 2-methoxyethyl, 2-ethoxyethyl, 2-carboxyethyl, 2-hydroxyethyl, 2-carbamoylethyl, 2-N-methylaminocarbonylethyl, 2-N,N-dimethylaminocarbonylethyl, 3-carboxypropyl, 4-hydroxybutyl, 5-hydroxypentyl, benzyl, etc.

When $R^7$ and $R^8$ are combined together to make a lower alkylene group, they form a 3- to 7-membered ring together with the nitrogen atom to which they are attached, and examples of the 3- to 7-membered ring are aziridine, azetidine, pyrrolidine, piperidine, etc.

Examples of the acid residue represented by X or $X^a$ are an inorganic acid residue (e.g. chlorine, bromine, fluorine, iodine), an organic acid residue (e.g. benzenesulfonyloxy, p-toluenesulfonyloxy, methanesulfonyloxy, trifluoromethanesulfonyloxy), etc.

The β-lactam compound (I) may be either in a free form or in a salt (preferably non-toxic salt) form. Examples of the salt are inorganic base salts (e.g. sodium, potassium, calcium, magnesium, ammonium), organic base salts (e.g. triethylammonium, pyridinium, diosopropylammonium), inorganic acid addition salts (e.g. hydrochloride, sulfate, phosphate), organic acid addition salts (e.g. formate, acetate, methanesulfonate, benzenesulfonate), etc.

Production of the β-lactam compound (I) will be hereinafter explained in details.

The quaternarization of the β-lactam compound (II) may be performed by a per se conventional procedure, for instance, by reacting the β-lactam compound (II) with the compound (III) in an inert solvent chosen from water, ketones (e.g. acetone, methylethylketone), ethers (e.g. tetrahydrofuran, dioxane), acetonitrile and halogenated hydrocarbons (e.g. dichloromethane, dichloroethane, chloroform), or their mixtures. There is no limitation on the reaction temperature, but the reaction is normally effected at a temperature of —40° to 60° C. Upon termination of the reaction, the objective product is isolated from the reaction mixture by a per se conventional procedure.

The thus obtained product, i.e. the β-lactam compound (IV), is optionally subjected to elimination of the hydroxyl-protecting group represented by $R^0$, elimination of the carboxyl-protecting group represented by $R^{2a}$ and/or elimination of the amino-protecting group represented by $R^{3a}$ to give the β-lactam compound (I) wherein at least one of $R^0$ and $R^3$ is a hydrogen atom and $R^2$ is a negative charge.

The elimination may be effected independently or concurrently by a per se conventional procedure such as treatment with an acid, a base, a reducing agent or the like (T. W. Greene: Protective Groups in Organic Synthesis, J. Wiley & Sons Inc., 1981). As the acid, there are exemplified trifluoroacetic acid, formic acid, boron trifluoride, aluminium chloride, etc. As the base, there are exemplified alkali metal carbonate (e.g. sodium carbonate, potassium carbonate), alkali metal sulfate (e.g. sodium sulfate, potassium sulfate), tetrafluorobutylammonium, etc. When the elimination is conducted through reduction, there may be adopted any procedure using zinc and acetic acid, hydrogen and palladium-carbon or platinum or the like. The elimination with tetrakistriphenylphosphine palladium is also available. Any particular limitation is not present on the solvent to be used, and it may be chosen from water, alcohols (e.g. methanol, ethanol), ethers (e.g. tetrahydrofuran, dioxane), aliphatic acids (e.g. acetic acid), etc. The reaction temperature may be appropiately decided so as to control or accelerate the proceeding of the reaction, and a preferred temperature is normally from $-30°$ to $40°$ C. The reaction product may be separated from the reaction mixture by a per se conventional procedure. For instance, the reaction mixture is neutralized and chromatographed on an adsorptive resin, followed by elution and lyophilization.

The β-lactam compound (II) as the starting compound is obtainable by reacting a β-lactam compound of the formula:

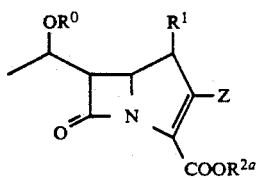

wherein $R^0$, $R^1$ and $R^{2a}$ are each as defined above and Z is a reactive ester on hydroxyl with a mercaptan compound of the formula:

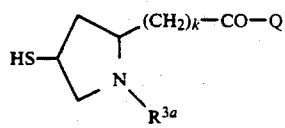

wherein $R^{3a}$, k and Q are each as defined above in an inert solvent in the presence of a base.

The β-lactam compound (V) is known (cf. Heterocycles, Vol. 21, p. 29–40, 1984), and its reactive ester on hydroxyl represented by Z may be chosen, for instance, from arylsulfonates such as benzenesulfonates and substituted benzenesulfonates (e.g. p-toluenesulfonate, p-nitrobenzenesulfonate, p-bromobenzenesulfonate), $C_1$-$C_5$ alkanesulfonates (e.g. methanesulfonate, ethanesulfonate), halo($C_1$-$C_5$)alkanesulfonates (e.g. trifluoromethanesulfonate), diarylphosphates (e.g. diphenylphosphate), halides (e.g. chloride, bromide, iodide), etc. Of these, p-toluenesulfuonate, methanesulfonate, diphenylphosphate, etc. are prefered.

The mercaptan compound (VI), which may be produced from trans-4-hydroxy-L-proline or cis-4-hydroxy-D-proline by a known method (cf. U.S. Pat. Nos. 4,943,569 and 4,962,103), is usually employed in an excessive amount, particularly in a 1 to 2 equivalent amount to the β-lactam compound (V) so that the reaction with the β-lactam compound (V) proceeds sufficiently.

Examples of the inert solvent are dioxane, tetrahydrofuran, dimethylsulfoxide, acetonitrile, hexamethylphosphoramide, etc. As the base, there may be used an inorganic base (e.g. sodium carbonate, potassium carbonate, sodium hydride, potassium hydride, potassium t-butoxide), an organic base (e.g. pyridine, dimethylaminopyridine, triethylamine, diisopropylethylamine, 1,8-diazabicyclo[5.4.0]-undec-7-ene (DBU), etc., among which preferred are diisopropylethylamine, DBU, etc. The base is used in such an amount as can assure the smooth proceeding of the reaction, normally in a 1 to 3 equimolar amount to the mercaptan compound (VI).

The reaction is normally carried out at a temperature of from $-78°$ to $60°$ C., preferably from $-40°$ to $40°$ C.

Upon termination of the reaction, the reaction mixture may be subjected to post-treatment in a per se conventional procedure so as to obtain the objective β-lactam compound (II) if necessary, followed by purification.

The β-lactam compound (I) of the invention includes asymmetric carbon atoms at the 4-, 5-, 6- and -positions in the carbapenem skeleton as shown in the following formula and has optical and steric isomers due to those asymmetric carbon atoms:

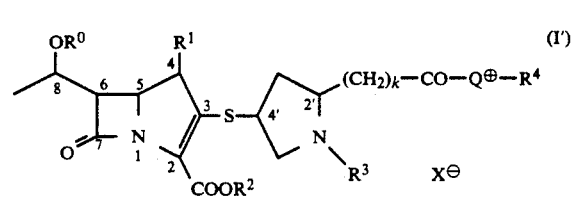

wherein $R^0$, $R^1$, $R^2$, $R^3$, $R^4$, k and $Q^\oplus$ and $X^\ominus$ are each as defined above. While all these optical and steric isomers and their mixtures fall within the scope of the invention, preferred are those having an S-configuration at the 5-position, i.e. (5S,6S) or (5S,6R), those having an R-configuration at the 8-position and those having an R configuration at the 4-position. More preferred are those having a (4R,5S,6S,8R) configuration as represented by the formula (I'-a) or a (4R,5S,6R,8R) configuration as represented by the formula (I'-b):

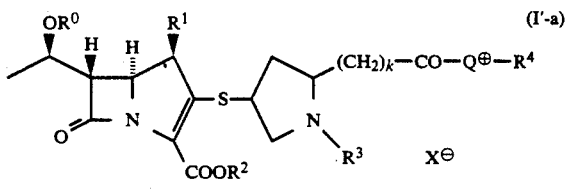

and

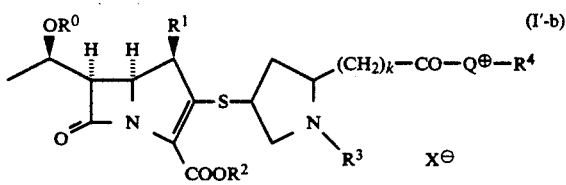

wherein $R^0$, $R^1$, $R^2$, $R^3$, $R^4$, k, and $Q^\oplus$ and $X^\ominus$ are each as defined most preferred are those of the formula (I'-c):

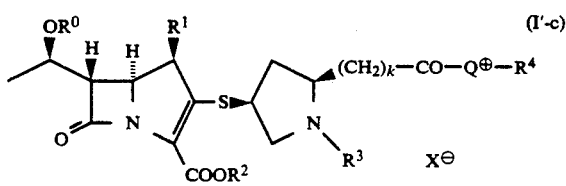

wherein $R^0$, $R^1$, $R^2$, $R^3$, $R^4$, k, $Q^\oplus$ and $X^\ominus$ are each as defined above.

Production of the specific isomers as above stated can be achieved by the use of the corresponding isomers of β-lactam compound (V) and the mercaptan compound (VI).

Typical examples of the β-lactam compound (I) wherein $R^0$ and $R^3$ are each a hydrogen atom, $R^1$ is a methyl group and $R^2$ is a negative charge are shown in Table 1, in which Me and Ph indicate respectively methyl and phenyl.

TABLE 1

[Core structure: carbapenem with OH-CH(Me)- on C6, methyl on C1, -S-(pyrrolidinyl with NH and (CH₂)ₖ-CO-Q⊕-R⁴ substituent) on C2, COO⁻ on C3]

| Compound No. | k | Q⊕ | R⁴ |
|---|---|---|---|
| 1 | 0 | 2-pyridinyl-NH- (H-N-pyridinium, N⊕ ortho) | Me |
| 2 | 0 | 2-pyridinyl-CH₂-NH- | Me |
| 3 | 0 | 2-pyridinyl-(CH₂)₂-NH- | Me |
| 4 | 0 | 2-pyridinyl-(CH₂)₃-NH- | Me |
| 5 | 0 | 2-pyridinyl-(CH₂)₄-NH- | Me |
| 6 | 0 | 2-pyridinyl-N(Me)- | Me |
| 7 | 0 | 2-pyridinyl-CH₂-N(Me)- | Me |
| 8 | 0 | 2-pyridinyl-(CH₂)₂-N(Me)- | Me |
| 9 | 0 | 2-pyridinyl-(CH₂)₃-N(Me)- | Me |
| 10 | 0 | 2-pyridinyl-(CH₂)₄-N(Me)- | Me |
| 11 | 0 | 3-pyridinyl-NH- | Me |
| 12 | 0 | 3-pyridinyl-CH₂-NH- | Me |
| 13 | 0 | 3-pyridinyl-(CH₂)₂-NH- | Me |
| 14 | 0 | 3-pyridinyl-(CH₂)₃-NH- | Me |
| 15 | 0 | 3-pyridinyl-(CH₂)₄-NH- | Me |
| 16 | 0 | 3-pyridinyl-N(Me)- | Me |
| 17 | 0 | 3-pyridinyl-CH₂-N(Me)- | Me |
| 18 | 0 | 3-pyridinyl-(CH₂)₂-N(Me)- | Me |
| 19 | 0 | 3-pyridinyl-(CH₂)₃-N(Me)- | Me |

TABLE 1-continued

[Structure: carbapenem with OH, Me substituents, S linked to pyrrolidine with NH, bearing (CH₂)ₖ—CO—Q⊕—R⁴, and COO⊖]

| Compound No. | k | Q⊕ | R⁴ |
|---|---|---|---|
| 20 | 0 | Me-N(H)-(CH₂)₄-[4-pyridinium] | Me |
| 21 | 0 | H-N-[4-pyridinium] | Me |
| 22 | 0 | H-N-CH₂-[4-pyridinium] | Me |
| 23 | 0 | H-N-(CH₂)₂-[4-pyridinium] | Me |
| 24 | 0 | H-N-(CH₂)₃-[4-pyridinium] | Me |
| 25 | 0 | H-N-(CH₂)₄-[4-pyridinium] | Me |
| 26 | 0 | Me-N-[4-pyridinium] | Me |
| 27 | 0 | Me-N-CH₂-[4-pyridinium] | Me |
| 28 | 0 | Me-N-(CH₂)₂-[4-pyridinium] | Me |
| 29 | 0 | Me-N-(CH₂)₃-[4-pyridinium] | Me |
| 30 | 0 | Me-N-(CH₂)₄-[4-pyridinium] | Me |
| 31 | 0 | H-N-CH₂-[3-pyridinium] | $CH_2Ph$ |
| 32 | 0 | H-N-CH₂-[3-pyridinium] | $CH_2COOH$ |
| 33 | 0 | H-N-CH₂-[3-pyridinium] | $CH_2CH_2OH$ |
| 34 | 0 | H-N-CH₂-[3-pyridinium] | $CH_2CONH_2$ |
| 35 | 0 | H-N-CH₂-[3-pyridinium] | $CH_2CONH$-Me |
| 36 | 0 | H-N-CH₂-[3-pyridinium] | $CH_2CON(Me)$-Me |
| 37 | 0 | H-N-CH₂-[3-pyridinium] | $CH_2CH_2CON(Me)$-Me |
| 38 | 0 | H-N-(CH₂)₂-[3-pyridinium] | $CH_2Ph$ |
| 39 | 0 | H-N-(CH₂)₂-[3-pyridinium] | $CH_2COOH$ |
| 40 | 0 | H-N-(CH₂)₂-[3-pyridinium] | $CH_2CH_2OH$ |
| 41 | 0 | H-N-(CH₂)₂-[3-pyridinium] | $CH_2CONH_2$ |

TABLE 1-continued

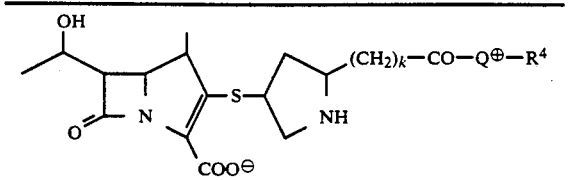

| Compound No. | k | Q⊕ | R⁴ |
|---|---|---|---|
| 42 | 0 | H-N-(CH₂)₂-[3-pyridinium] | CH₂CONH-Me |
| 43 | 0 | H-N-(CH₂)₂-[3-pyridinium] | CH₂CON(Me)-Me |
| 44 | 0 | H-N-(CH₂)₂-[3-pyridinium] | CH₂CH₂CON(Me)-Me |
| 45 | 0 | Me-N-(CH₂)₂-[3-pyridinium] | PhCH₂ |
| 46 | 0 | Me-N-(CH₂)₂-[3-pyridinium] | CH₂COOH |
| 47 | 0 | Me-N-(CH₂)₂-[3-pyridinium] | CH₂CH₂OH |
| 48 | 0 | Me-N-(CH₂)₂-[3-pyridinium] | CH₂CONH₂ |
| 49 | 0 | Me-N-(CH₂)₂-[3-pyridinium] | CH₂CONH-Me |
| 50 | 0 | Me-N-(CH₂)₂-[3-pyridinium] | CH₂CON(Me)-Me |
| 51 | 0 | Me-N-(CH₂)₂-[3-pyridinium] | CH₂CH₂CON(Me)-Me |
| 52 | 0 | H-N-(CH₂)₃-[4-pyridinium] | CH₂Ph |

TABLE 1-continued

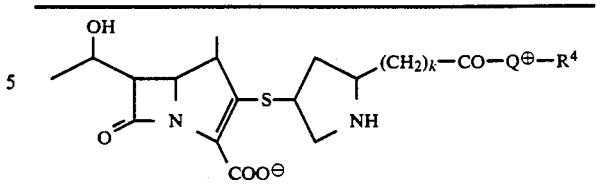

| Compound No. | k | Q⊕ | R⁴ |
|---|---|---|---|
| 53 | 0 | H-N-(CH₂)₃-[4-pyridinium] | CH₂COOH |
| 54 | 0 | H-N-(CH₂)₃-[4-pyridinium] | CH₂CH₂OH |
| 55 | 0 | H-N-(CH₂)₃-[4-pyridinium] | CH₂CONH₂ |
| 56 | 0 | H-N-(CH₂)₃-[4-pyridinium] | CH₂CONH-Me |
| 57 | 0 | H-N-(CH₂)₃-[4-pyridinium] | CH₂CON(Me)-Me |
| 58 | 0 | H-N-(CH₂)₃-[4-pyridinium] | CH₂CH₂CON(Me)-Me |
| 59 | 0 | Me-N-(CH₂)₃-[4-pyridinium] | CH₂Ph |
| 60 | 0 | Me-N-(CH₂)₃-[4-pyridinium] | CH₂COOH |
| 61 | 0 | Me-N-(CH₂)₃-[4-pyridinium] | CH₂CH₂OH |
| 62 | 0 | Me-N-(CH₂)₃-[4-pyridinium] | CH₂CONH₂ |
| 63 | 0 | Me-N-(CH₂)₃-[4-pyridinium] | CH₂CONH-Me |

TABLE 1-continued

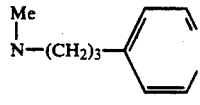

| Compound No. | k | Q⊕ | R⁴ |
|---|---|---|---|
| 64 | 0 | Me-N(CH₂)₃-[pyridinium-4-yl] | CH₂CON(Me)Me |
| 65 | 0 | Me-N(CH₂)₃-[pyridinium-4-yl] | CH₂CH₂CON(Me)Me |
| 66 | 1 | H-N-CH₂-[pyridinium-3-yl] | Me |
| 67 | 1 | H-N-(CH₂)₂-[pyridinium-3-yl] | Me |
| 68 | 1 | H-N-(CH₂)₃-[pyridinium-4-yl] | Me |
| 69 | 1 | Me-N-(CH₂)₃-[pyridinium-4-yl] | Me |
| 70 | 2 | H-N-CH₂-[pyridinium-3-yl] | Me |
| 71 | 2 | H-N-(CH₂)₂-[pyridinium-3-yl] | Me |
| 72 | 2 | H-N-(CH₂)₃-[pyridinium-4-yl] | Me |
| 73 | 2 | Me-N-(CH₂)₃-[pyridinium-4-yl] | Me |
| 74 | 0 | CH₂CH₂OH-N-CH₂-[pyridinium-3-yl] | Me |
| 75 | 0 | CH₂CH₂OH-N-(CH₂)₂-[pyridinium-3-yl] | Me |
| 76 | 0 | CH₂CH₂OH-N-(CH₂)₂-[pyridinium-4-yl] | Me |
| 77 | 0 | CH₂CH₂OH-N-(CH₂)₃-[pyridinium-4-yl] | Me |
| 78 | 0 | H-N-(CH₂)₂-[5-methylpyridinium-2-yl] | Me |
| 79 | 0 | H-N-(CH₂)₂-[3-methylpyridinium-2-yl] | Me |
| 80 | 0 | Me-N-(CH₂)₃-[4-methylpyridinium-3-yl] | Me |
| 81 | 0 | Me-N-(CH₂)₃-[2-methylpyridinium-4-yl] | Me |
| 82 | 0 | N-methylpiperazinium | Me |
| 83 | 0 | N-methylpiperazinium | CH₂Ph |
| 84 | 0 | N-methylpiperazinium | CH₂COOH |
| 85 | 0 | N-methylpiperazinium | CH₂CH₂OH |

TABLE 1-continued

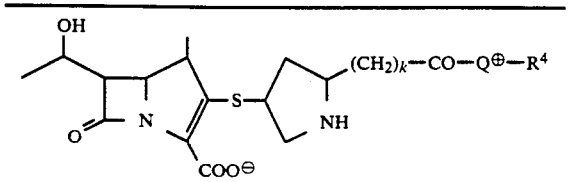

| Compound No. | k | Q⊕ | R⁴ |
|---|---|---|---|
| 86 | 0 | N∧N⊕—Me (piperazinium) | CH₂CONH₂ |
| 87 | 0 | N∧N⊕—Me | CH₂CONH—Me |
| 88 | 0 | N∧N⊕—Me | CH₂CON(Me)—Me |
| 89 | 0 | N∧N⊕—Me | CH₂CH₂CON(Me)—Me |
| 90 | 1 | N∧N⊕—Me | Me |
| 91 | 1 | N∧N⊕—Me | CH₂Ph |
| 92 | 1 | N∧N⊕—Me | CH₂COOH |
| 93 | 1 | N∧N⊕—Me | CH₂CH₂OH |
| 94 | 1 | N∧N⊕—Me | CH₂CONH₂ |
| 95 | 1 | N∧N⊕—Me | CH₂CONH—Me |
| 96 | 1 | N∧N⊕—Me | CH₂CON(Me)—Me |
| 97 | 1 | N∧N⊕—Me | CH₂CH₂CON(Me)—Me |
| 98 | 0 | N⌒—N⊕(Me)—Me (piperidinyl) | Me |
| 99 | 0 | N⌒—CH₂—N⊕(Me)—Me | Me |
| 100 | 0 | N⌒—(CH₂)₂—N⊕(Me)—Me | Me |
| 101 | 1 | N⌒—N⊕(Me)—Me | Me |
| 102 | 1 | N⌒—CH₂—N⊕(Me)—Me | Me |
| 103 | 1 | N⌒—(CH₂)₂—N⊕(Me)—Me | Me |
| 104 | 0 | N⌒—(CH₂)—N⊕(pyrrolidinyl) | Me |
| 105 | 0 | N⌒—(CH₂)₂—N⊕(piperidinyl) | Me |
| 106 | 0 | N∧N⊕—Me | CH₂CH₂CN |
| 107 | 0 | N∧N⊕—Me | CH₂CH₂OMe |

TABLE 1-continued

Structure: carbapenem core with OH-CH(Me)- substituent, N, O, COO⁻, linked via S to pyrrolidine with NH–(CH₂)ₖ–CO–Q⊕–R⁴

| Compound No. | k | Q⊕ | R⁴ |
|---|---|---|---|
| 108 | 0 | piperazinium: N / N⊕—Me | CH₂CO—Me |
| 109 | 0 | Me–N–(CH₂)₃–pyridinium (N⊕) | CH₂CH₂CN |
| 110 | 0 | Me–N–(CH₂)₃–pyridinium (N⊕) | CH₂CH₂OMe |
| 111 | 0 | Me–N–(CH₂)₃–pyridinium (N⊕) | CH₂CO—Me |
| 112 | 0 | H–N–CH₂–piperidinium (N⊕—Me) | Me |
| 113 | 0 | H–N–(CH₂)₂–piperidinium (N⊕—Me) | Me |
| 114 | 0 | Me–N–(CH₂)₂–piperidinium (N⊕—Me) | Me |
| 115 | 0 | Me–N–(CH₂)₂–piperidinium (N⊕—Me) | CH₂COOH |
| 116 | 0 | Me–N–(CH₂)₂–piperidinium (N⊕—Me) | CH₂CH₂OH |
| 117 | 0 | Me–N–(CH₂)₂–piperidinium (N⊕—Me) | CH₂CONH₂ |
| 118 | 1 | Me–N–(CH₂)₂–piperidinium (N⊕—Me) | CH₂CO—Me |

The β-lactam compounds as exemplified in Table 1 have their optical and steric isomers, and all of them are included within the scope of the present invention.

The β-lactam compounds (I) according to the invention are characteristic in having a 2-substituted pyrrolidin-4-ylthio group introduced with a quaternary ammonium group at the 3-position and a lower alkyl group at the 4-position in the carbapenem skeleton. Due to such characteristic structure, the β-lactam compounds (I) exert an excellent antimicrobial activity against Gram-positive and Gram-negative bacteria including Staphylococcus aureus, Streptococcus pyogenes, Escherichia coli, Serratia marcescens, Pseudomonas aeruginosa, etc. It is notable that while conventional carbapenem compounds such as imipenem are generally unstable in a living body, especially sensitive to renal DHP-I, the β-lactam compounds (I), particularly those wherein $R^1$ is a methyl group in the R-configuration, are in general significantly resistant to renal DHP-I. It is also notable that the half life time (T½) of the β-lactam compounds (I) in a living body is generally longer than that of conventional carbapenem compounds such as imipenem. The β-lactam compounds (I) are thus useful as antimicrobial drugs or intermediates in the synthesis of such antimicrobial drugs.

For the practical usage of the β-lactam compounds (I) as antimicrobial drugs, they may be formulated into conventional preparation forms together with excipients or additives such as carriers, diluents, binders and stabilizers and administered in various modes, of which examples are oral administration in the form of tablets, capsules, dispersants and syrups, non-oral administration in the form of injection through vein, muscle or rectum, etc. When they are applied in injection forms, the preparations may additionally include buffering agents, solubilizing agents, isotonic agents, etc. The daily dosage may vary depending upon the state of disease, the age and body weight of patients, the administration mode and time, etc., and the normal daily dosage to a human adult is between about 100 to 3000 mg, optionally divided in one to several times per day. If necessary, the dosage may be increased or decreased appropriately.

Practical and presently preferred embodiments of the invention are illustratively shown in the following examples, which are not intended to limit the scope of the invention thereto. Further, the abbreviations used therein show the following meanings: PNZ, p-nitrobenzyloxycarbonyl; PNB, p-nitrobenzyl; Ph, phenyl; Ac, acetyl; TBDMS, t-butyldimethylsilyl; Me, methyl, etc.

EXAMPLE 1

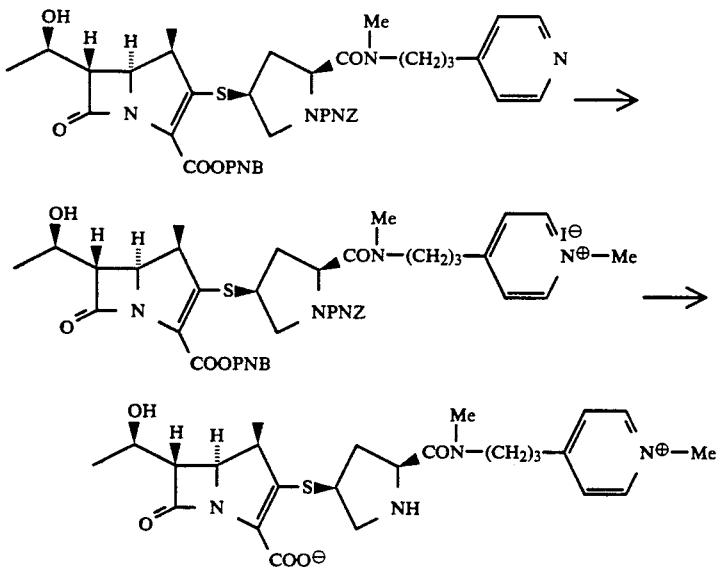

To a solution of (4R,5S,6S,8R,2'S,4'S)-p-nitrobenzyl-3-[1-p-nitrobenzyloxycarbonyl-2-(3-(4-pyridyl)-propyl) methylaminocarbonyl)pyrrolidin-4-ylthio]-4-methyl-6-(1-hydroxyethyl) -1-azabicyclo[3.2.0]hept-2-en-7-one-2-carboxylate (100 mg) in acetone (2.0 ml), methyl iodide (1.14 g) was added, and the resultant mixture was stirred at room temperature for 20 hours, followed by removal of the solvent under reduced pressure. The residue was dissolved in tetrahydrofuran (5.0 ml) and 0.1 M phosphate buffer (pH, 7.0; 5.0 ml), and 10 % palladium-carbon (150 mg) was added thereto. Catalytic reduction was performed at room temperature for 1.5 hours under atmospheric pressure of hydrogen. The catalyst was removed by filtration, and the filtrate was washed with dichloromethane three times. After removal of the solvent from the washed filtrate under reduced pressure, the residue was purified by polymer chromatography (CHP-20P) using 2 % aqueous tetrahydrofuran as an eluent. The eluted fractions were collected and freeze-dried to give (4R,5S,6S,8R,2'S,4'S)-3-[2-((3-(1-methylpyridinium-4-yl)propyl) methylaminocarbonyl)pyrrolidin-4-ylthio]-4-methyl-6-(1-hydroxyethyl) -1-azabicyclo[3.2.0]hept-2-en-7-one-2-carboxylate.

UV$_{max}$ nm (H$_2$O): 257, 263 (sh), 298;
IR$_{max}$ cm$^{-1}$ (KBr): 3400, 1737, 1682, 1367;
NMR δ (D$_2$O): 1.18 (3H, d, J =7.3 Hz), 1.26 (3H, d, J =6.6 Hz), 3.04 (3H, s), 4.20 (3H, s), 7.87 (2H, d, J=6.6 Hz), 8.60 (2H, d, J=6.6 Hz).

EXAMPLE 2

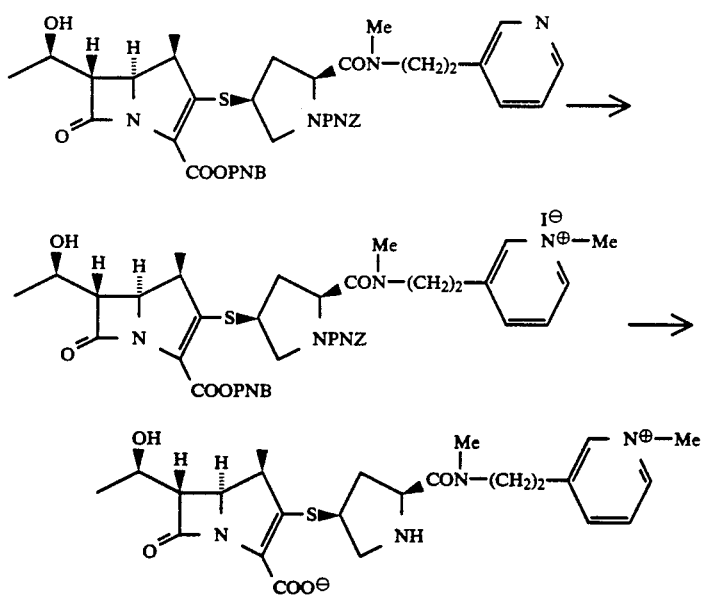

To a solution of (4R,5S,6S,8R,2'S,4'S)-p-nitrobenzyl-3-[1-p-nitrobenzyloxycarbonyl-2-((2-(3-pyridyl)ethyl) methylaminocarbonyl)pyrrolidin-4-ylthio]-4-methyl-6-(1-hydroxyethyl) -1-azabicyclo[3.2.0]hept-2-en-7-one-2-carboxylate (270 mg) in acetone (25 ml), methyl iodide (3.42 g) was added, and the resultant mixture was stirred at room temperature for 3 hours, followed by removal of the solvent under reduced pressure. The residue was dissolved in tetrahydrofuran (15 ml) and 0.1 M phosphate buffer (pH, 7.0; 15.0 ml), and 10 % palladium-carbon (500 mg) was added thereto. Catalytic reduction was performed at room temperature for 1 hour under atmospheric pressure of hydrogen. The reaction mixture was subjected to post-treatment int he same manner as in Example 1. the filtrate was purified by polymer chromatography (CHP-20P) using 2% aqueous tetrahydrofuran as an eluent to give (4R,5S,6S,8R,2′S, 4′S)-3-[2-((2-methylpyridinium -3-yl)ethyl)methylaminocarbonyl)pyrrolidin-4-ylthio]-4-methyl-6-(1-hydroxyethyl)-1-azabicyclo[3.2.0]-hept-2-en-7-one-2-carboxylate.

$UV_{max}$ nm ($H_2O$): 268, 273, 298;

$IR_{max}$ cm$^{-1}$ (KBr): 3320, 1748, 1637, 1585, 1378;

NMR δ ($D_2O$): 1.20 (3H, d, J=7.3 Hz), 1.27 (3H, d, J=6.3 Hz), 2.81 (1H, m), 3.00–3.30 (5H, m), 3.09 (3H, s), 3.45 (3H, m), 3.79 (1H, m), 4.20 (4H, m), 4.38 (3H, s), 7.98 (1H, dd, J=6.3 and 8.3 Hz), 8.44 (1H, d, J=8.3 Hz), 8.69 (1H, d, J=6.3 Hz), 8.79 (1H, s).

EXAMPLE 3

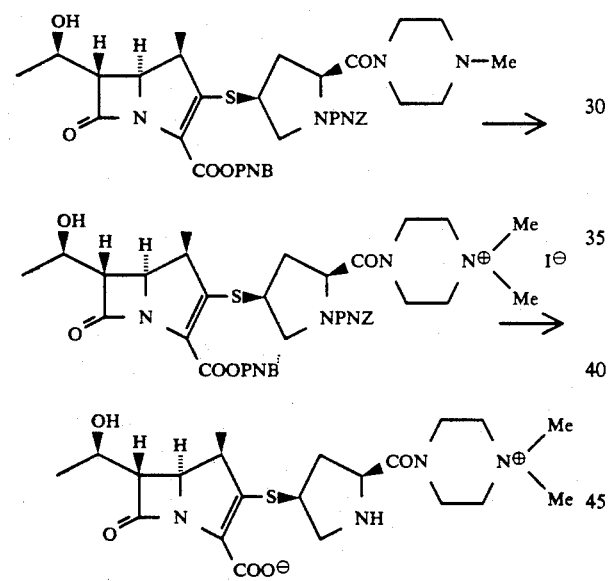

To a solution of (4R, 5S, 6S, 8R, 2′S, 4′S)-p-nitrobenzyl-3-[1-p-nitrobenzyloxycarbonyl-2-(4-methylpiperazin-1-ylcarbonyl) pyrrolidin-4-ylthiol]-04-methyl-6-(1-hydroxyethyl) -1-azabicyclo[3.2.0]hept-2-en-7-one-2-carboxylate (200 mg) in acetone (2.0 ml), methyl iodide (1.14 g) was added, and the resultant mixture was stirred at room temperature for 20 hours, followed by removal of the solvent under reduced pressure. The residue was dissolved in tetrahydrofuran (10.0 ml) and 0.1 M phosphate buffer (pH, 7.0; 10.0 ml), and 10% palladium-carbon (241 mg) was added thereto. Catalytic reduction was performed at room temperature for 1.5 hours under atmospheric pressure of hydrogen. The reaction mixture was subjected to post-treatment in the same manner as in Example 1. The filtrate was purified by polymer chromatography (CHP-20P) using 1 % aqueous tetrahydrofuran as an eluent to give (4R,5S,6S,8R,2′S,4′S)-3-[2-(4,4-dimethylpiperazinium-1-yl-carbonyl)pyrrolidin-4-ylthio]-4-methyl-6-(1-hydroxyethyl)-1-azabicyclo[3.2.0]-hept -2-en-7-one-2-carboxylate.

$UV_{max}$ nm ($H_2O$): 299;

$IR_{max}$ cm$^{-1}$ (KBr): 3440, 1745, 1640, 1587, 1464, 1387, 1260;

NMR δ ($D_2O$): 1.21 (3H, d, J=7.3 Hz), 1.29 (3H, d, J=6.6 Hz), 1.72 (1H, m), 2.78 (1H, m), 3.11 (1H, dd, J=4.0 & 12.5 Hz), 3.27 (6H, s), 3.20–3.60 (9H, m), 3.80–4.20 (5H, m), 4.23 (3H, m).

EXAMPLES 4 TO 22

In the same manner as above, the compounds as shown in Table 2 were obtained. The physical properties of the compounds as obtained follow the Table.

TABLE 2

| Example No. | k | $Q^⊕$ | $R^4$ |
|---|---|---|---|
| 4 | 0 | H−N−⟨pyridinium⟩ | —Me |
| 5 | 0 | H−N−CH₂−⟨pyridinium⟩ | —Me |
| 6 | 0 | H−N−(CH₂)₂−⟨pyridinium⟩ | —Me |
| 7 | 0 | H−N−(CH₂)₃−⟨pyridinium⟩ | —Me |
| 8 | 0 | H−N−(CH₂)₄−⟨pyridinium⟩ | —Me |
| 9 | 0 | Me−N−(CH₂)₃−⟨pyridinium⟩ | —Me |
| 10 | 0 | Me−N−(CH₂)₄−⟨pyridinium⟩ | —Me |
| 11 | 0 | H−N−⟨pyridinium⟩ | —Me |

TABLE 2-continued

[Structure: carbapenem core with OH-CH(CH3)- side chain, H, CH3, COO⁻, and S-pyrrolidine-NH substituent bearing (CH2)k—CO—Q⊕—R⁴ group]

| Example No. | k | Q⊕ | R⁴ |
|---|---|---|---|
| 12 | 0 | —NH—CH₂—(4-pyridinium) | —Me |
| 13 | 0 | —NH—(CH₂)₃—(4-pyridinium) | —Me |
| 14 | 0 | —N(Me)—(CH₂)₂—(4-pyridinium) | —Me |
| 15 | 1 | —NH—(CH₂)₂—(3-pyridinium) | —Me |
| 16 | 2 | —NH—(3-pyridinium) | —Me |
| 17 | 0 | —N(CH₂CH₂OH)—CH₂—(3-pyridinium) | —Me |
| 18 | 1 | —N(piperazinium)—Me | —Me |
| 19 | 0 | —NH—(CH₂)₂—(4-Me-piperidinium) | —Me |
| 20 | 1 | —NH—(CH₂)₂—(1-Me-piperidinium-4-yl) | —Me |
| 21 | 0 | —N(piperidinyl)—CH₂CH₂N⊕(Me)—Me | —Me |
| 22 | 0 | —N(piperazinium)—(CH₂)₂—OH | —Me |

Physical Properties

EXAMPLE 4

UV$_{max}$ nm (H₂O): 252, 291;
IR$_{max}$ cm⁻¹ (KBr): 3380, 1737, 1580, 1502, 1364;
NMR δ (D₂O): 1.19 (3H, d, J=7.3 Hz), 1.29 (3H, d, J=6.3 Hz), 1.95 (1H, m), 2.73 (1H, m), 3.00 (1H, dd, J=4.6 & 11.9 Hz), 3.40 (3H, m), 3.79 (1H, m), 4.09 (1H, dd, J=5.6 & 9.6 Hz), 4.25 (2H, m), 4.40 (3H, s), 7.99 (1H, dd, J=6.3 & 8.6 Hz), 8.47 (1H, d, J=8.6 Hz), 8.53 (1H, d, J=6.3 Hz), 9.27 (1H, s).

EXAMPLE 5

UV$_{max}$ nm (H₂O): 265, 273 (sh), 296;
IR$_{max}$ cm⁻¹ (KBr): 3360, 1730, 1670, 1590, 1385;
NMR δ (D₂O): 1.19 (3H, d, J=7.3 Hz), 1.25 (1H, m), 1.27 (3H, d, J=6.3 Hz), 2.17 (1H, m), 3.02 (1H, m), 3.30–3.85 (4H, m), 4.08 (1H, m), 4.22 (2H, m), 4.37 (3H, s), 4.65 (3H, m), 8.02 (1H, t, J=7.9 Hz), 8.46 (1H, d, J=8.3 Hz), 8.71 (1H, d, J=6.0 Hz), 8.77 (1H, s).

EXAMPLE 6

UV$_{max}$ nm (H₂O): 266, 272, 299;
IR$_{max}$ cm⁻¹ (KBr): 3300, 1750, 1652, 1588, 1380, 1366;
NMR δ (D₂O): 1.19 (3H, d, J=7.3 Hz), 1.29 (3H, d, J=6.3 Hz), 1.49 (1H, m), 2.69 (1H, m), 2.91 (1H, dd, J=4.5 & 11.9 Hz), 3.10 (2H, t, J=6.6 Hz), 3.30–3.50 (3H, m), 3.63 (2H, t, J =5.9 Hz), 3.75 (1H, m), 3.93 (1H, dd, J=6.3 & 9.6 Hz), 4.20–4.30 (2H, m), 4.37 (3H, s), 7.99 (1H, dd, J=6.2 & 8.0 Hz), 8.44 (1H, d, J=8.0 Hz), 8.67 (1H, d, J=6.2 Hz), 8.77 (1H, s).

EXAMPLE 7

UV$_{max}$ nm (H₂O): 266, 273 (sh), 299;
IR$_{max}$ cm⁻¹ (KBr): 3410, 1749, 1640, 1588, 1380, 1278, 1255, 1178, 1140;
NMR δ (D₂O): 1.19 (3H, d, J=7.3 Hz), 1.29 (3H, d, J=6.3 Hz), 1.75 (1H, m), 1.96 (2H, m), 2.69 (1H, m), 2.89 (2H, m), 2.95 (1H, dd, J=4.3 & 11.9 Hz), 3.20–3.50 (5H, m), 3.75 (1H, m), 3.87 (1H, dd, J=6.3 & 9.5 Hz), 4.20 (2H, m), 4.35 (3H, s), 7.94 (1H, t, J=7.0 Hz), 8.38 (1H, d, J=7.9 Hz), 8.61 (1H, d, J=6.0 Hz), 8.68 (1H, s).

EXAMPLE 8

UV$_{max}$ nm (H₂O): 266, 273, 299;
NMR δ (D₂O): 1.19 (3H, d, J=7.0 Hz), 1.30 (3H, d, J=6.6 Hz), 1.61 (2H, m), 1.73 (3H, m), 2.72 (1H, m), 2.89 (2H, m), 2.99 (1H, dd, J=4.6 & 11.9 Hz), 3.29 (2H, m), 3.43 (3H, m), 3.79 (1H, m), 3.92 (1H, dd, J=6.3 & 9.2 Hz), 4.23 (2H, m), 4.34 (3H, s), 7.93 (1H, dd, J=6.3 & 8.3 Hz), 8.39 (1H, d, J=8.3 Hz), 8.59 (1H, d, J=6.3 Hz), 8.68 (1H, s).

EXAMPLE 9

UV$_{max}$ nm (H₂O): 268, 273, 297;
IR$_{max}$ cm⁻¹ (KBr): 3425, 1744, 1632, 1588, 1380, 1281;
NMR δ (D₂O): 1.21 (3H, d, J=7.3 Hz), 1.30 (3H, d, J=6.3 Hz), 1.82 (1H, m), 1.98 (2H, m), 2.86 (3H, m), 3.09 (3H, s), 3.20–3.70 (6H, m), 3.95 (1H, m), 4.24 (2H, m), 4.36 (3H, s), 4.48 (1H, dd, J=6.9 & 9.6 Hz), 7.97 (1H, t, J=7.0 Hz), 8.42 (1H, d, J=7.6 Hz), 8.62 (1H, d, J=6.3 Hz), 8.70 (1H, s).

EXAMPLE 10

UV$_{max}$ nm (H$_2$O): 268, 276, 296;

IR$_{max}$ cm$^{-1}$ (KBr): 3425, 1746, 1636, 1592, 1378, 1282, 1246;

NMR δ (D$_2$): 1.18 (3H, d, J=7.3 Hz), 1.28 (3H, d, J=6.3 Hz), 1.66 (4H, m), 1.86 (1H, m), 2.93 (3H, m), 3.03 (3H, s), 3.20-3.80 (7H, m), 4.01 (1H, m), 4.23 (2H, m), 4.32 (3H, s), 7.92 (1H, t, J=7.0 Hz), 8.39 (1H, d, J=7.5 Hz), 8.56 (1H, d, J=6.2 Hz), 8.65 (1H, s).

EXAMPLE 11

UV$_{max}$ nm (H$_2$O): 273, 300;

IR$_{max}$ cm$^{-1}$ (KBr): 3400, 1777, 1730, 1618;

NMR δ (D$_2$O): 1.20 (3H, d, J=7.3 Hz), 1.28 (3H, d, J=6.6 Hz), 2.14 (1H, m), 2.68 (1H, m), 2.94 (1H, m), 3.25-3.50 (3H, m), 3.63 (1H, dd, J=6.3 & 11.9 Hz), 3.73 (1H, m), 4.02 (1H, m), 4.23 (3H, s), 4.47 (1H, m), 8.10 (2H, d, J=7.3 Hz), 8.57 (2H, d, J=7.3 Hz).

EXAMPLE 12

UV$_{max}$ nm (H$_2$O): 258, 263 (sh), 297;

IR$_{max}$ cm$^{-1}$ (KBr): 3420, 1743, 1638, 1582, 1381;

NMR δ (D$_2$O): 1.19 (3H, d, J=7.3 Hz), 1.28 (3H, d, J=6.6 Hz), 1.91 (1H, m), 2.76 (1H, m), 3.06 (1H, dd, J=4.0 & 11.9 Hz), 3.43 (3H, m), 3.80 (1H, m), 4.10 (1H, dd, J=5.9 & 9.7 Hz), 4.21 (2H, m), 4.34 (3H, s), 4.68 (1H, d, J=18.2 Hz), 4.70 (1H, d, J=18.2 Hz), 7.90 (2H, d, J=6.3 Hz), 8.69 (2H, d, J=6.3 Hz).

EXAMPLE 13

UV$_{max}$ nm (H$_2$O): 256, 263, 299;

IR$_{max}$ cm$^{-1}$ (KBr): 3410, 1743, 1639, 1584, 1376;

NMR δ (D$_2$O): 1.20 (3H, d, J=7.3 Hz), 1.31 (3H, d, J=6.3 Hz), 1.79 (1H, m), 2.01 (2H, m), 2.72 (1H, m), 2.99 (3H, m), 3.20-3.50 (5H, m), 3.79 (1H, m), 3.92 (1H, m), 4.30 (2H, m), 4.33 (3H, s), 7.89 (2H, d, J=6.6 Hz), 8.62 (2H, d, J=6.6 Hz).

EXAMPLE 14

UV$_{max}$ nm (H$_2$O): 257, 263 (sh), 300;

NMR δ (D$_2$O): 1.18 (3H, d, J=7.3 Hz), 1.26 (3H, d, J=6.3 Hz), 1.80 (1H, m), 2.77 (1H, m), 3.05 (3H, s), 4.28 (3H, s), 7.93 (2H, d, J=6.6 Hz), 8.64 (2H, d, J=6.6 Hz).

EXAMPLE 15

UV$_{max}$ nm (H$_2$O): 269, 273, 296;

IR$_{max}$ cm$^{-1}$ (KBr): 3380, 1742, 1652, 1580, 1370, 1239, 1008;

NMR δ (D$_2$O): 1.18 (3H, d, J=6.9 Hz), 1.26 (3H, d, J=6.3 Hz), 1.92 (1H, m), 2.42 (1H, m), 2.56 (2H, m), 3.04 (3H, m), 3.25-3.70 (5H, m), 3.80 (1H, m), 3.96(1H, m), 4.26 (2H, m), 4.35 (3H, s), 7.95 (1H, t, J=7.6 Hz), 8.40 (1H, d, J=8.6 Hz), 8.65 (1H, d, J=6.0 Hz), 8.72 (1H, s).

EXAMPLE 16

UV$_{max}$ nm (H$_2$O): 249, 294;

NMR δ (D$_2$O): 1.21 (3H, d, J=6.9 Hz), 1.29 (3H, d, J=6.3 Hz), 1.70 (1H, m), 2.15 (2H, m), 2.73 (2H, m), 3.20-3.50 (3H, m), 3.50-3.85 (3H, m), 4.10 (1H, m), 4.18 (2H, m), 4.38 (3H, s), 7.92 (1H, m), 8.37 (1H, d, J=7.9 Hz), 8.51 (1H, d, J=5.9 Hz), 9.27 (1H, s).

EXAMPLE 17

UV$_{max}$ nm (H$_2$O): 267, 272, 300;

IR$_{max}$ cm$^{-1}$ (KBr): 3410, 1746, 1638, 1586, 1383;

NMR δ (D$_2$O): 1.22 (3H, d, J=7.3 Hz), 1.30 (3H, d, J=6.3 Hz), 1.70 (1H, m), 2.85 (1H, m), 3.12 (1H, dd, J=3.6 & 12.2 Hz), 3.25 (1H, dd, J=5.3 & 12.2 Hz), 3.43 (2H, m), 3.70-3.90 (5H, m), 4.24 (2H, m), 4.39 (1H, m), 4.40 (3H, s), 4.80 (1H, d, J=16.5 Hz), 4.92 (1H, d, J=16.5 Hz), 8.03 (1H, dd, J=6.5 & 7.9 Hz), 8.43 (1H, d, J=7.9 Hz), 8.71 (2H, m).

EXAMPLE 18

UV$_{max}$ nm (H$_2$O): 297;

IR$_{max}$ cm$^{-1}$ (KBr): 3400, 1748, 1639, 1586, 1453, 1372, 1257, 1088;

NMR δ (D$_2$): 1.17 (3H, d, J=7.3 Hz), 1.24 (3H, d, J=6.3 Hz), 1.49 (1H, m), 2.61 (1H, m), 2.90 (2H, d, J=6.9 Hz), 3.08 (1H, dd, J=3.3 & 12.5 Hz), 3.21 (6H, s), 3.30-3.60 (7H, m), 3.73 (1H, t, J=7.3 Hz), 3.90 (5H, m), 4.20 (2H, m).

EXAMPLE 19

UV$_{max}$ nm (H$_2$O): 300;

IR$_{max}$ cm$^{-1}$ (KBr): 3410, 1744, 1650, 1588, 1485, 1381, 1250, 1206, 1092;

NMR δ (D$_2$O): 1.22 (3H, d, J=7.0 Hz), 1.31 (3H, d, J=6.3 Hz), 1.70 (6H, m), 2.00 (2H, m), 2.74 (1H, m), 3.04 (1H, dd, J=5.0 & 12.2 Hz), 3.08 (3H, s), 3.15 (3H, s), 3.25-3.60 (9H, m), 3.81 (1H, m), 3.97 (1H, dd, J=6.4 & 9.5 Hz), 4.24 (2H, m).

EXAMPLE 20

UV$_{max}$ nm (H$_2$O): 297;

IR$_{max}$ cm$^{-1}$ (KBr): , 1742, 1635, 1582, 1479, 1363, 1241, 1201, 1082;

NMR δ (D$_2$O): 1.28 (3H, d, J=7.3 Hz), 1.30 (3H, d, J=6.3 Hz), 1.70 (6H, m), 1.97 (2H, m), 2.72 (1H, m), 2.79 (1H, m), 3.08 (3H, s), 3.15 (3H, s), 3.23-3.70 (10H, m), 4.02 (2H, m), 4.31 (2H, m).

EXAMPLE 21

UV$_{max}$ nm (H$_2$O): 295;

IR$_{max}$ cm$^{-1}$ (KBr): 3440, 1758, 1644, 1597, 1492, 1379,

NMR δ (D$_2$O): 1.21 (3H, d, J=7.0 Hz), 1.29 (3H, d, J=6.6 Hz), 1.80 (7H, m), 2.86 (1H, m), 3.02 (1H, m), 3.11 (9H, s), 3.18 (2H, m), 3.39 (5H, m), 3.60 (1H, m), 3.80 (1H, m), 3.99 (1H, m), 4.24 (2H, m), 4.34 (1H, m), 4.64 (1H, m).

EXAMPLE 22

UV$_{max}$ nm (H$_2$O): 297;

IR$_{max}$ cm$^{-1}$ (KBr): 3400, 1743, 1637, 1588, 1380;

NMR δ (D$_2$O): 1.22 (3H, d, J=6.9 Hz), 1.30 (3H, d, J=6.3 Hz), 1.68 (1H, m), 3.10 (1H, dd, J=4.0 & 12.5 Hz), 2.76 (1H, m), 3.24 (1H, dd, J=5.4 & 12.5 Hz), 3.31 (3H, s), 3.43 (2H, m), 3.68 (8H, m) 3.86 (1H, m), 3.97 (2H, m), 4.12 (2H, m ), 4.25 (3H, m).

EXAMPLE 23

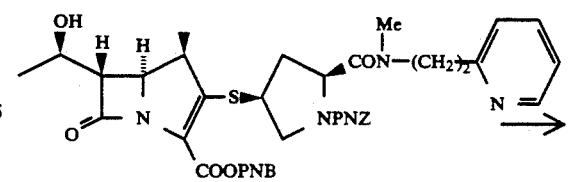

-continued

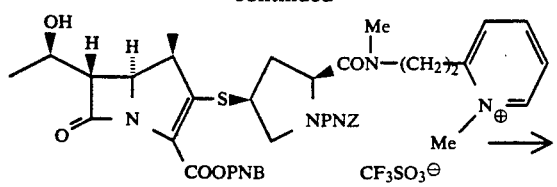

A solution of (4R,5S,6S,8R,2'S,4'S)-p-nitrobenzyl-3-[1-(p-nitrobenzyloxycarbonyl)-2-((2-(2-pyridyl)-ethyl)methylaminocarbonyl)pyrrolidin-4-ylthio]-4-methyl-6-(1-hydroxyethyl)-1-azabicyclo[3.2.0]hept-2-en-7-one-2-carboxylate (208 mg) in dry dichloromethane (3.0 ml) was stirred under ice-cooling, and methyl trifluoromethanesulfonate (64 mg) was dropwise added thereto, followed by stirring at the same temperature for 1 hour. The reaction mixture was combined with tetrahydrofuran (10.0 ml), 0.1 M phosphate buffer (pH, 7.0; 10.0 ml) and 10 % palladium-carbon (350 mg), and catalytic reduction was performed at room temperature for 1 hour under atmospheric pressure of hydrogen. The reaction mixture was subjected to post-treatment in the same manner as in Example 1. The filtrate was purified by polymer chromatography (CHP-20P) using 2% aqueous tetrahydrofuran as an eluent to give (4R,5S,6S,8R,2'S,4'S)-3-[2-((2-(1-methylpyridinium-2-yl)-ethyl) methylaminocarbonyl)pyrrolidin-4-ylthio]-4-methyl-6-(1-hydroxyethyl)-1-azabicyclo[3.2.0]hept-2-en-7-one-2-carboxylate.

UV$_{max}$ nm (H$_2$O): 269, 274, 298;

IR$_{max}$ cm (KBr): 3450, 1737, 1625, 1580, 1372, 1251, 1153;

NMR δ (D$_2$O): 1.20 (3H, d, J=7.2 Hz), 1.28 (3H, d, J=6.3 Hz), 1.60 (1H, m), 3.00 (1H, m), 3.16 (3H, s), 3.26 (1H, dd, J 3.3 & 12.2 Hz), 3.30–3.60 (5H, m), 3.65 (1H, m), 3.94 (1H, m), 4.13 (1H, m), 4.23 (2H, m), 4.40 (3H, s), 4.52 (1H, dd, J =7.2 & 9.9 Hz), 7.90 (1H, d, J=7.9 Hz), 7.92 (1H, t, J=6.0 Hz), 8.45 (1H, t, J=7.9 Hz), 8.76 (1H, d, J=6.0 Hz).

EXAMPLES 24 TO 31

In the same manner as in Example 23, the compounds as shown in Table 3 were obtained. The physical properties of the compounds as obtained follow the Table.

TABLE 3

| Example No. | k | Q⊕ | R⁴ |
|---|---|---|---|
| 24 | 0 | H−N−CH₂−(2-pyridinium) | —Me |
| 25 | 0 | H−N−(CH₂)₂−(2-pyridinium) | —Me |
| 26 | 0 | Me−N−(CH₂)₃−(2-pyridinium) | —Me |
| 27 | 0 | H−N−(CH₂)₂−(5-Me-2-pyridinium) | —Me |
| 28 | 0 | Me on pyridinium, N−(CH₂)₂−(3-Me-2-pyridinium) | —Me |
| 29 | 0 | H−N−(CH₂)₂−(4-pyridinium) | —Me |
| 30 | 0 | piperazinium −N⊕−(CH₂)₃−OH | —Me |
| 31 | 0 | piperazinium −N⊕−(CH₂)₂−OMe | —Me |

Physical Properties

EXAMPLE 24

UV$_{max}$ nm (H$_2$O): 267, 274 (sh), 298;

IR$_{max}$ cm$^{-1}$ (KBr): 3430, 1743, 1679, 1577, 1380, 1260, 1158;

NMR δ (D$_2$O): 1.21 (3H, d, J=7.3 Hz), 1.28 (3H, d, J=6.3 Hz), 2.20 (1H, m), 3.03 (1H, m), 3.03–3.60 (3H, m), 3.76 (1H, dd, J=6.3 & 12.2 Hz), 4.07 (1H, m), 4.23 (2H, m), 4.34 (3H, s), 4.64 (1H, dd, J=6.6 & 8.9 Hz), 4.89 (1H, d, J=18.2 Hz), 4.90 (1H, d, J=18.2 Hz), 7.95 (1H, t, J=7.0 Hz) 7.96 (1H, d, J=8.0 Hz), 8.52 (1H, t, J=8.0 Hz), 8.79 (1H, d, J=6.3 Hz).

EXAMPLE 25

UV$_{max}$ nm (H$_2$O): 268, 273 (sh), 297;

IR$_{max}$ cm$^{-1}$ (KBr): 3440, 1750, 1672, 1630, 1580, 1379, 1270;

NMR δ (D$_2$): 1.19 (3H, d, J=7.3 Hz), 1.28 (3H, d, J=6.3 Hz), 1.88 (1H, m), 2.89 (1H, m), 3.30–3.50 (5H, m), 3.70 (2H, m), 3.85 (1H, dd, J=6.9 & 14.2 Hz), 4.00 (1H, m), 4.24 (2H, m), 4.36 (3H, s), 4.41 (1H, dd, J=6.6 & 9.6 Hz), 7.90 (2H, m), 8.46 (1H, t, J=6.6 Hz), 8.76 (1H, d, J =6.1 Hz).

EXAMPLE 26

$UV_{max}$ nm ($H_2O$): 267, 273 (sh), 296;

$IR_{max}$ cm$^{-1}$ (KBr): 3450, 1745, 1640, 1584, 1380, 1255, 1159;

NMR δ ($D_2O$): 1.21 (3H, d, J=6.9 Hz , 1.30 (3H, d, J=6.3 Hz), 2.03 (1H, m), 2.14 (2H, m), 3.20–3.30 (3H, m), 3.19 (3H, s), 3.30–3.70 (4H, m), 3.80 (2H, m), 4.10 (1H, m), 4.28 (2H, m), 4.30 (3H, s), 7.86 (1H, t, J=6.6 Hz), 7.98 (1H, d, J=8.3 Hz), 8.45 (1H, t, J=7.6 Hz), 8.72 (1H, d, J=5.6 Hz).

EXAMPLE 27

$UV_{max}$ nm ($H_2O$): 296, 270 (sh), 265;

$IR_{max}$ cm$^{-1}$ (KBr): 1578, 1441, 1378, 1267, 1246, 1157;

NMR δ ($D_2O$): 1.21 (3H, d, J=7.2 Hz), 1.30 (3H, d, J=6.6 Hz), 1.78 (1H, m), 2.75 (3H, s), 2.90 (1H, m), 3.09 (2H, m), 3.30–3.60 (5H, m), 3.68 (1H, dd, J=6.0 & 12.2 Hz), 3.79 (1H, m), 4.01 (1H, m), 4.21 (3H, s), 4.23 (2H, m), 4.42 (1H, dd, J=6.0 & 9.6 Hz), 7.87 (1H, d, J=7.9 Hz), 8.30 (1H, dd, J=1.3 & 7.9 Hz), 8.68 (1H, d, J=1.3 Hz).

EXAMPLE 28

$UV_{max}$ nm ($H_2O$): 278, 296;

$IR_{max}$ cm$^{-1}$ (KBr): 3430, 1753, 1677, 1592, 1450, 1382, 1278, 1254, 1224, 1156;

NMR δ ($D_2O$): 1.22 (3H, d, J=7.3 Hz), 1.30 (3H, d, J=6.6 Hz), 1.81 (1H, m), 2.83 (3H, s), 2.89 (1H, m), 3.17 (2H, m), 3.38 (2H, m), 3.50 (2H, m), 3.72 (2H, m), 4.00 (1H, m), 4.24 (2H, m), 4.28 (3H, s), 4.39 (1H, dd, J=6.6 & 9.3 Hz), 7.80 (1H, t, J=7.2 Hz), 8.29 (1H, d, J=7.6 Hz), 8.63 (1H, d, J=5.3 Hz).

EXAMPLE 29

$UV_{max}$ nm ($H_2O$): 300, 264, 257, 228;

$IR_{max}$ cm$^{-1}$ (KBr): 3400 (br), 1746, 1640, 1582, 1381, 1266;

NMR δ ($D_2$): 1.21 (3H, d, J=7.3 Hz), 1.30 (3H, d, J=6.3 Hz), 1.56 (1H, m), 2.73 (1H, m), 2.97 (1H, dd, J=4.6 & 12.2 Hz), 3.20 (2H, m), 3.40 (3H, m), 3.75 (1H, m), 4.00 (1H, dd, J=6.0 & 9.6 Hz) 4.24 (3H, m), 4.34 (3H, s), 7.95 (2H, d, J=6.6 Hz), 8.69 (2H, d, J=6.6 Hz).

EXAMPLE 30

$UV_{max}$ nm ($H_2O$): 294;

$IR_{max}$ cm$^{-1}$ (KBr): 3400, 1749, 1640, 1588, 1382, 1252;

NMR δ ($D_2$): 1.22 (3H, d, J=7.3 Hz), 1.31 (3H, d, J=6.6 Hz), 1.76 (1H, m), 2.10 (2H, m), 2.81 (1H, m), 3.20 (2H, m), 3.24 (3H, s), 3.43 (1H, m), 3.61 (7H, m), 3.73 (2H, m), 3.92 (3H, m), 4.27 (5H, m).

EXAMPLE 31

$UV_{max}$ nm ($H_2O$): 292;

$IR_{max}$ cm$^{-1}$ (KBr): 3430, 1752, 1640, 1592, 1390, 1260;

NMR δ ($D_2O$): 1.24 (3H, d, J=7.3 Hz), 1.32 (3H, d, J=6.3 Hz), 1.69 (1H, m), 2.80 (1H, m), 3.12 (1H, dd, J=3.3 & 12.9 Hz), 3.24 (1H, dd, J=5.0 & 12.9 Hz), 3.31 (3H, s), 3.43 (3H, s), 3.44 (2H, m), 3.52–4.10 (13H, m), 4.29 (3H, m).

EXAMPLE 32

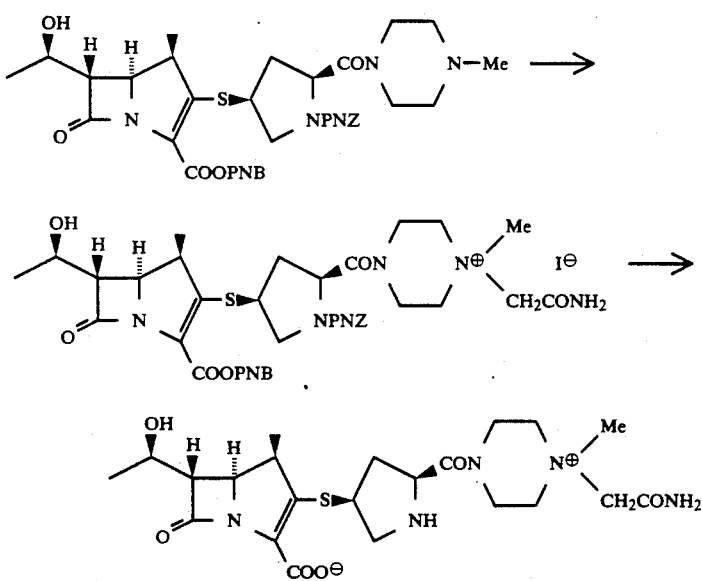

To a solution of (4R,5S,6S,8R,2'S,4'S)-p-nitrobenzyl-3-[1-p-nitrobenzyloxycarbonyl -2-(4-methylpiperazin-1-ylcarbonyl)pyrrolidin-4-ylthio]-4-methyl-6-(1-hydroxyethyl)-1-azabicyclo [3.2.0]hept-2-en-7-one-2-carboxylate (200 mg) in acetone (3.0 ml), iodoacetamide (200 mg) was added at room temperature, and the resultant mixture was stirred at the same temperature for 20 hours and concentrated under reduced pressure. The residue was combined with ethyl acetate (20 ml), stirred and allowed to stand. After removal of the supernatant by decantation, the insoluble material was dissolved in tetrahydrofuran (10 ml) and 0.1 M -phosphate buffer (pH, 7.0; 10 ml), followed by addition of palladium-carbon (430 mg). Catalytic reduction was performed at room temperature for 2 hours under ordinary or autogenic pressure. The reaction mixture was subjected to post-treatment in the same manner as in Example 1. The filtrate was purified by polymer chromatography (CHP-20P) using 1 % aqueous tetrahydrofuran as an eluent to give (4R,5S,6S,8R,2'S,4'S)-3-[2-(4-aminocarbonylmethyl-4-methylpiperazinium -1-ylcarbonyl)pyrrolidin-4-ylthio]-4-ylthio]-4-methyl-6-(1-hydroxyethyl)-1-azabicyclo [3.2.0]hept-2-en-7-one-2-carboxylate.

$UV_{max}$ nm (H$_2$O): 297;

$IR_{max}$ cm$^{-1}$ (KBr): 3400, 1740, 1692, 1652, 1441, 1400, 1253, 1177, 1136;

NMR δ (D$_2$O): 1.23 (3H, d, J=7.3 Hz), 1.29 (3H, d, J=6.3 Hz), 2.05 (1H, m), 3.10 (1H, m), 3.45 (3H, s , 3.48 (3H, m), 3.70–4.40 (13H, m).

EXAMPLES 33 TO 37

In the same manner as in Example 32, the compounds as shown in Table 4 were obtained. The physical properties of the compounds obtained follow the Table.

TABLE 4

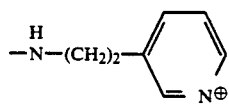

| Example No. | k | $Q^{\oplus}$ | $R^4$ |
|---|---|---|---|
| 33 | 0 | 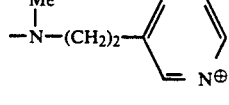 | —CH$_2$CONH$_2$ |
| 34 | 0 | 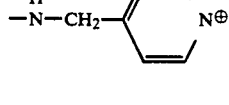 | —CH$_2$CONH$_2$ |
| 35 | 0 | 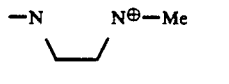 | —CH$_2$CONH$_2$ |
| 36 | 1 | —N\_\_\_N$^{\oplus}$—Me | —CH$_2$CONH$_2$ |
| 37 | 0 | 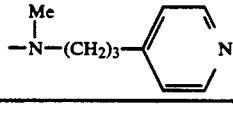 | —CH$_2$CONH$_2$ |

Physical Properties

EXAMPLE 33

$UV_{max}$ nm (H$_2$O): 273, 294;

$IR_{max}$ cm$^{-1}$ (KBr): 3380, 1742, 1677, 1580, 1434, 1380, 1275, 1242;

NMR δ (D$_2$O): 1.20 (3H, d, J=7.3 Hz), 1.29 (3H, d, J=6.3 Hz), 1.77 (1H, m), 2.80 (1H, m), 3.14 (2H, m), 3.33 (2H, m), 3.45 (1H, dd, J=2.6 & 6.3 Hz), 3.50–3.75 (2H, m), 3.78 (1H, dd, J=6.3 & 13.5 Hz), 4.20–4.40 (3H, m), 5.50 (2H, s), 8.09 (1H, dd, J=6.3 & 8.3 Hz), 8.58 (1H, d, J=8.3 Hz), 8.70 (1H, d, J=6.3 Hz), 8.78 (1H, s).

EXAMPLE 34

$UV_{max}$ nm (H$_2$O): 271, 294;

$IR_{max}$ cm$^{-1}$ (KBr): 3390, 1751, 1693, 1638, 1592, 1378;

NMR δ (D$_2$O): 1.20 (3H, d, J=7.3 Hz), 1.28 (3H, d, J=6.3 Hz), 1.54 (1H, m), 3.02 (1H, m), 3.03 (3H, s), 3.22 (2H, m), 3.36 (2H, m), 3.46 (1H, dd, J=2.6 & 5.9 Hz), 3.61 (2H, m), 3.97 (1H, m), 4.12 (1H, m), 4.24 (2H, m), 4.74 (1H, m), 5.50 (2H, s), 8.08 (1H, dd, J=6.3 & 8.2 Hz), 8.60 (1H, d, J=8.2 Hz), 8.71 (1H, d, J=6.3 Hz), 8.79 (1H, s).

EXAMPLE 35

$UV_{max}$ nm (H$_2$O): 259, 265 (sh), 297;

$IR_{max}$ cm$^{-1}$ (KBr): 3400, 1748, 1682, 1639, 1545, 1388, 1279;

NMR δ (D$_2$O): 1.23 (3H, d, J=7.3 Hz), 1.29 (3H, d, J=6.3 Hz), 2.28 (1H, m), 3.05 (1H, m), 3.35–3.60 (3H, m), 3.84 (1H, dd, J=7.3 & 12.2 Hz), 4.10–4.45 (3H, m), 5.51 (2H, s), 8.02 (2H, d, J=7.0 Hz) 8.75 (2H, d, J =7.0 Hz).

EXAMPLE 36

$UV_{max}$ nm (H$_2$O): 297;

$IR_{max}$ cm$^{-1}$ (KBr): 3380, 1747, 1687, 1636, 1586, 1444, 1378, 1244, 1089;

NMR δ (D$_2$O): 1.17 (3H, d, J=7.3 Hz), 1.24 (3H, d, J=6.3 Hz), 1.54 (1H, m), 2.63 (1H, m), 2.93 (2H, br.d, J=6.6 Hz), 3.12 (1H, br.d, J=12.5 Hz), 3.37 (3H, s), 4.23 (4H, m).

EXAMPLE 37

$UV_{max}$ nm (H$_2$O): 299, 263 (sh), 256, 226 (sh);

$IR_{max}$ cm$^{-1}$ (KBr): 3400, 1746, 1691, 1637, 1584, 1387;

NMR δ (D$_2$O): 1.22 (3H, d, J=7.3 Hz), 1.31 (3H, d, J=6.3 Hz), 1.62 (1H, m), 2.13 (2H, m), 2.86 (1H, m), 3.03 (2H, m), 3.08 (3H, s), 3.22 (2H, m), 3.45 (3H, m), 3.66 (1H, m), 3.87 (1H, m), 4.28 (3H, m), 5.52 (2H, s), 8.00 (2H, d, J=6.9 Hz), 8.68 (2H, d, J=6.9 Hz).

EXAMPLES 38 TO 47

In the same manner as in Example 32 but using different alkylating agents (Y) in place of iodoacetamide, the compounds as shown in Table 5 were obtained. The physical properties of the compounds obtained follow the Table.

TABLE 5

[Structure: carbapenem core with OH-isopropyl group, β-lactam, COO⁻, and thio-pyrrolidine-NH substituent with (CH₂)ₖ—CO—Q⊕—R⁴ side chain]

| Example No. | Y | k | Q⊕ | R⁴ |
|---|---|---|---|---|
| 38 | BrCH₂CONH—Me | 0 | —N⌬N⊕—Me (piperazine) | —CH₂CONH—Me |
| 39 | BrCH₂CON(Me)₂ | 0 | —N⌬N⊕—Me (piperazine) | —CH₂CON(Me)₂ |
| 40 | ICH₂CH₂CON(Me)₂ | 0 | —N⌬N⊕—Me (piperazine) | —CH₂CH₂CON(Me)₂ |
| 41 | BrCH₂COOPNB | 0 | —N⌬N⊕—Me (piperazine) | —CH₂COOH |
| 42 | ICH₂COOH | 0 | —NH—CH₂—(4-pyridinium) | —CH₂COOH |
| 43 | PhCH₂Br | 0 | —NH—CH₂—(3-pyridinium) | —CH₂Ph |
| 44 | BrCH₂COMe | 0 | —N(Me)—(CH₂)₃—(4-pyridinium) | —CH₂COMe |
| 45 | ICH₂CH₂OH | 0 | —N(Me)—(CH₂)₃—(4-pyridinium) | —CH₂CH₂OH |
| 46 | BrCH₂CO—Me | 0 | —N⌬N⊕—Me (piperazine) | —CH₂CO—Me |
| 47 | BrCH₂COOPNB | 0 | —N⌬N⊕—(CH₂)₂—OH (piperazine) | —CH₂COOH |

Physical Property

EXAMPLE 38

UV$_{max}$ nm (H₂O): 299;
IR$_{max}$ cm$^{-1}$ (KBr): 3410, 1736, 1638, 1362;
NMR δ (D₂O): 1.19 3H, d, J=7.3 Hz), 1.26 (3H, d, J=6.3 Hz), 2.77 (3H, s), 3.15 (1H, dd, J=3.3 & 12.2 Hz), 3.28 (1H, dd, J=4.4 & 12.2 Hz), 3.38 (3H, s).

EXAMPLE 39

UV$_{max}$ nm (H₂O): 296;
IR$_{max}$ cm$^{-1}$ (KBr): 3400, 1746, 1644, 1589, 1378, 1253;
NMR δ (D₂O): 1.22 (3H, d, J=7.3 Hz), 1.30 (3H, d, J=6.3 Hz), 1.71 (1H, m), 2.78 (1H, m), 2.98 (3H, s), 3.05

(3H, s), 3.13 (1H, dd, J=3.6 & 12.2 Hz), 3.25 (1H, dd, J=4.0 & 12.2 Hz), 3.46 (3H, s), 4.53 (2H, br. s).

EXAMPLE 40

UV$_{max}$ nm (H$_2$O): 297;

IR$_{max}$ cm$^{-1}$ (KBr): 3430, 1745, 1633, 1583, 1480, 1369, 1242, 1087;

NMR δ (D$_2$O): 1.22 (3H, d, J=7.3 Hz), 1.31 (3H, d, J=6.6 Hz), 1.93 (1H, m), 2.96 (3H, s), 3.11 (3H, s), 3.26 (3H, s).

EXAMPLE 41

UV$_{max}$ nm (H$_2$O): 298;

IR$_{max}$ cm$^{-1}$ (KBr): 3420, 1745, 1627, 1592, 1448, 1382, 1254;

NMR δ (D$_2$O): 1.23 (3H, d, J=7.3 Hz), 1.30 (3H, d, J=6.3 Hz), 1.82 (1H, m), 2.92 (1H, m), 3.42 (3H, s).

EXAMPLE 42

UV$_{max}$ nm (H$_2$O): 258, 266 (sh), 292;

NMR δ (D$_2$O): 1.22 (3H, d, J=7.3 Hz), 1.29 (3H, d, J=6.3 Hz), 2.21 (1H, m), 3.01 (1H, m), 3.38 (1H, m), 3.49 (3H, m) 3.79 (1H, dd, J=6.6 & 12.2 Hz), 4.10 (1H, m), 4.26 (2H, m), 4.66 (2H, m), 5.21 (2H, s), 7.97 (2H, d, J=6.9 Hz), 8.71 (2H, d, J=6.9 Hz).

EXAMPLE 43

UV$_{max}$ nm (H$_2$O): 261, 266, 298;

IR$_{max}$ cm$^{-1}$ (KBr): 3400, 1753, 1672, 1596, 1367;

NMR δ (D$_2$O): 1.15 (3H, d, J=7.3 Hz), 1.30 (3H, d, J=6.6 Hz), 1.85 (1H, m), 2.72 (1H, m), 3.10–4.00 (5H, m), 4.25 (3H, m), 4.59 (1H, d, J=15.9 Hz), 4.68 (1H, d, J 15.9 Hz), 5.84 (2H, s), 7.60 (5H, m), 8.07 (1H, t, J=7.9 Hz), 8.51 (1H, d, J=8.5 Hz), 8.81 (1H, s), 8.87 (1H, d, J=5.9 Hz).

EXAMPLE 44

UV$_{max}$ nm (H$_2$O): 299, 264 (sh), 257, 230;

IR$_{max}$ cm$^{-1}$ (KBr): 3410 (br), 1745, 1638, 1593, 1378;

NMR δ (D$_2$O): 1.22 (3H, d, J=7.6 Hz), 1.31 (3H, d, J=6.3 Hz), 1.66 (1H, m), 2.16 (2H, m), 2.44 (3H, s), 2.90 (1H, m), 3.07 (3H, s), 3.68 (1H, m), 3.87 (1H, m), 4.27 (4H, m), 8.00 (2H, d, J=6.9 Hz), 8.53 (2H, d, J =6.9 Hz).

EXAMPLE 45

UV$_{max}$ nm (D$_2$O): 296, 261, 255, 223;

IR$_{max}$ cm$^{-1}$ (KBr): 3425, 1751, 1639, 1592, 1304;

NMR δ (D$_2$O): 1.23 (3H, d, J=7.3 Hz), 1.32 (3H, d, J=6.3 Hz), 1.62 (1H, m), 2.12 (2H, m), 2.86 (1H, m), 2.97 (2H, m), 3.09 (3H, s), 3.20 (2H, m), 3.44 (4H, m), 3.62 (1H, m), 3.90 (1H, m), 4.08 (2H, m), 4.26 (4H, m), 7.97 (2H, d, J=6.6 Hz), 8.72 (2H, d, J=6.6 Hz).

EXAMPLE 46

UV$_{max}$ nm (H$_2$O): 296;

IR$_{max}$ cm$^1$ (KBr): 3400(br), 1743, 1724, 1630, 1593,

NMR δ (D$_2$O): 1.20 (3H, d, J=7.3 Hz), 1.28 (3H, d, J=6.3 Hz), 1.70 (1H, m), 2.26 (3H, s), 2.77 (1H, m), 3.07 (1H, dd, J=12.5 & 3.6 Hz), 3.19 (1H, dd, J=12.5 & 6.6 Hz), 3.39 (3H, s), 3.40 (1H, m), 3.60–4.10 (11H, m), 4.23 (4H, m).

EXAMPLE 47

UV$_{max}$ nm (H$_2$O): 297;

IR$_{max}$ cm$^1$ (KBr): 3400 (br), 1742, 1624, 1590, 1382;

NMR δ (D$_2$O): 1.24 (3H, d, J=7.3 Hz), 1.31 (3H, d, J=6.3 Hz), 1.85 (1H, m), 2.92 (1H, m), 3.28 (1H, m), 3.47 (5H, m), 3.80–4.37 (15H, m), 4.52 (1H, m).

REFERENCE EXAMPLE 1

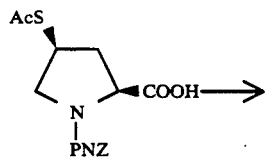

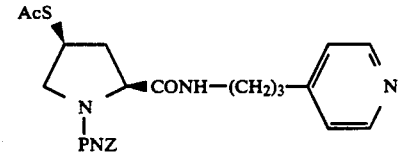

To a solution of cis-1-(p-nitrobenzyloxycarbonyl)-4-acetylthio-L-proline (552 mg; 1.5 mmol) and triethylamine (303 mg; 3.0 mmol) in dry tetrahydrofuran (6 ml), a solution of ethyl chloroformate (184 mg; 1.7 mmol) in dry tetrahydrofuran (1.5 ml) was dropwise added under ice-cooling, followed by stirring for 0.5 hour. To the reaction mixture, 4-(3-aminopropyl)pyridine (306 mg; 2.25 mmol) was added, and the resultant mixture was stirred for 1 hour. The reaction mixture was diluted with ethyl acetate, washed with aqueous sodium hydrogen carbonate solution and aqueous sodium chloride solution in order and dried over anhydrous magensium sulfate-anhydrous sodium carbonate. After removal of the solvent, the residue was purified by silica gel chromatography to give (2S,4S)-1-(p-nitrobenzyloxycarbonyl)-2-[3-(4-pyridylpropyl) aminocarbonyl]-4-acetylthiopyrrolidine.

IR$_{max}$ cm$^{-1}$ (neat): 3300 (br), 1693, 1602, 1520, 1400, 1340, 1107;

NMR δ (CDCl$_3$): 2.32 (3H, s), 2.4–2.8 (4H, m), 3.2–3.5 (3H, m), 3.9–4.1 (1H, m), 4.1–4.2 (1H, m), 4.3 4.4 (1H, m), 5.25 (2H, s), 6.66 (1H, br.s), 7.10 (2H, d, J=5.0 Hz), 7.49 (2H, d, J=7.6 Hz), 8.20 (2H, d, J =8.3 Hz), 8.49 (2H, m).

REFERENCE EXAMPLES 2 TO 16

In the same manner as in Reference Example 1, the thioacetates as shown in Table 6 were obtained from the corresponding amines. The physical properties of the compounds obtained follow the Table.

TABLE 6

AcS—[pyrrolidine with N-PNZ]—(CH$_2$)$_k$—CO—Q

| Reference Example No. | (CH$_2$)$_k$—CO—Q |
|---|---|
| 2 | —CON(H)—[4-pyridyl] |

TABLE 6-continued

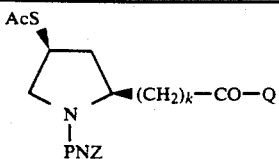

| Reference Example No. | (CH₂)ₖ—CO—Q |
|---|---|
| 3 | 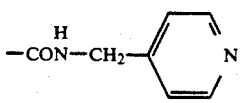 |
| 4 | 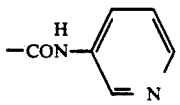 |
| 5 | 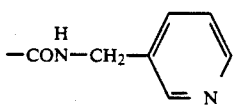 |
| 6 | 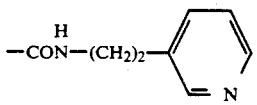 |
| 7 | 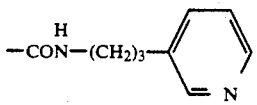 |
| 8 | 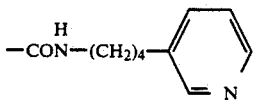 |
| 9 | 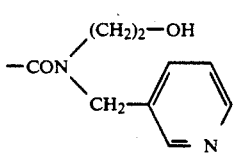 |
| 10 | 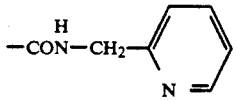 |
| 11 | 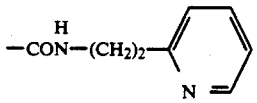 |
| 12 | 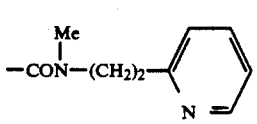 |
| 13 | 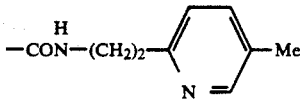 |

TABLE 6-continued

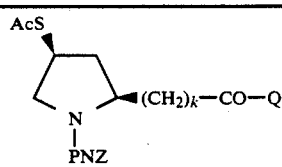

| Reference Example No. | (CH₂)ₖ—CO—Q |
|---|---|
| 14 | 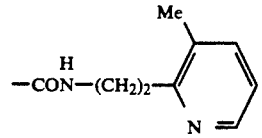 |
| 15 | 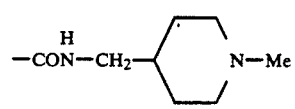 |
| 16 | 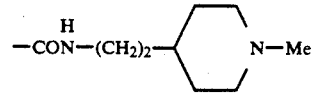 |

Physical Properties

REFERENCE EXAMPLE 2

$IR_{max}$ cm$^{-1}$ (neat): 3310, 1700, 1592, 1523, 1402, 1340, 1290, 1211, 1182, 1162, 1118;

NMR δ (CDCl₃): 2.34 (3H, s), 2.54 (2H, m), 3.45 (1H, m), 4.03 (1H, m), 4.16 (1H, dd, J=10.9 & 7.0 Hz), 4.54 (1H, m), 5.31 (2H, m), 7.39 (2H, d, J=6.0 Hz), 7.52 (2H, m), 8.22 (2H, m), 8.41 (2H, m), 9.58 (1H, br. s).

REFERENCE EXAMPLE 3

$IR_{max}$ cm$^{-1}$ (KBr): 1706, 1695, 1663, 1598, 1513, 1432, 1415, 1403, 1343, 1177, 1122;

NMR δ (CDCl₃): 2.32 (3H, s), 2.55 (2H, m), 3.42 (1H, dd, J=11.6 & 6.0 Hz), 4.01 (1H, quint., J=6.9 Hz), 4.12 (1H, dd, J=11.2 & 6.6 Hz), 4.46 (3H, m), 5.23 (2H, s), 7.19 (2H, m), 7.49 (2H, m), 8.21 (2H, d, J=8.6 Hz), 8.52 (2H, m).

REFERENCE EXAMPLE 4

NMR δ (CDCl₃): 2.17 (3H, s), 2.5–2.9 (2H, m), 3.45 (1H, m), 4.03 (1H, m), 4.16 (1H, dd, J=11.2 & 6.9 Hz), 4.56 (1H, m), 5.31 (2H, m), 7.22 (1H, m), 7.52 (2H, m), 8.05 (1H, m), 8.22 (2H, m), 8.32 (1H, m), 8.56 (1H, br. s).

REFERENCE EXAMPLE 5

NMR δ (CDCl₃): 2.32 (3H, s), 2.4–2.7 (2H, m), 3.40 (1H, dd, J=11.2 & 5.9 Hz), 3.99 (1H, m), 4.11 (1H, dd, J=11.2 & 6.9 Hz), 4.40 (3H, m), 5.21 (2H, br. s), 7.25 (1H, m), 7.48 (2H, m), 7.61 (1H, m), 8.19 (2H, m), 8.51 (2H, m).

REFERENCE EXAMPLE 6

$IR_{max}$ cm$^{-1}$ (neat): 3270, 1700 (sh), 1660, 1508, 1395, 1333, 1100;

NMR δ (CDCl₃): 2.33 (3H, s), 2.70–3.00 (2H, m), 3.20–3.70 (3H, m), 3.70–4.40 (3H, m), 5.21 (2H, m), 6.83 (1H, br. s), 7.10–7.40 (1H, m), 7.4–7.7 (3H, m), 8.22 (2H, d, J=8.3 Hz), 8.46 (2H, m).

REFERENCE EXAMPLE 7

IR$_{max}$ cm$^{-1}$ (neat): 3280, 2920, 1700 (sh), 1660 (br), 1510, 1390, 1330, 1100;

NMR δ (CDCl$_3$): 1.75–2.0 (2H, m), 2.32 (3H, s), 2.4–2.8 (3H, m), 3.15–3.6 (3H, m), 3.99 (1H, t, J=6.6 Hz), 4.05 –4.25 (1H, m), 4.3–4.5 (1H, m), 5.25 (1H, s), 6.66 (1H, br. s), 7.4 –7.7 (3H, m), 8.20 (2H, d, J=7.9 Hz), 8.45 (2H, d, J=4.6 Hz).

REFERENCE EXAMPLE 8

IR$_{max}$ cm$^{-1}$ (neat): 3300 (br), 1718, 1707 (sh), 1690, 1520, 1422, 1400, 1342, 1112;

NMR δ (CDCl$_3$): 1.35–1.8 (4H, m), 2.31 (3H, s), 2.4–2.8 (4H, m), 3.2–3.5 (3H, m), 3.90–4.05 (1H, m), 4.05–4.2 (1H, m), 4.34 (1H, dd, J=5.6 & 8.3 Hz), 5.23 (2H, s), 6.57 (1H, br. s), 7.1–7.3 (1H, m), 7.3–7.7 (3H, m), 8.22 (2H, d, J=8.3 Hz), 8.44 (2H, m).

REFERENCE EXAMPLE 9

IR$_{max}$ cm$^{-1}$ (CHCl$_3$): 3400 (br), 1690, 1685 (sh), 1655, 1521, 1422, 1345, 1200, 1120;

NMR δ (CDCl$_3$): 2.35 (3H, s), 3.2–3.6 (3H, m), 3.6–4.8 (8H, m), 4.8–5.2 (2H, m), 5.24 (2H, s), 7.2–7.5 (1H, m), 7.51 (2H, d, J=8.9 Hz), 7.6–7.8 (1H, m), 8.23 (2H, d, J=8.9 Hz), 8.4–8.7 (2H, m).

REFERENCE EXAMPLE 10

IR$_{max}$ cm$^{-1}$ (KBr): 3310, 1767, 1700, 1653, 1518, 1435, 1344, 1260, 1240, 1172, 1098;

NMR δ (CDCl$_3$): 2.28 (1H, m), 2.30 (3H, s), 2.75 (1H, m), 3.44 (1H, m), 3.99 (1H, m), 4.21 (1H, m), 4.53 (3H, m), 5.12 (1H, m), 5.24 (2H, br. s), 7.2 –7.7 (5H, m), 8.0 (1H, m), 8.23 (1H, m), 8.51 (1H, m).

REFERENCE EXAMPLE 11

NMR δ (CDCl$_3$): 2.20 (1H, m), 2.28 (3H, s), 2.98 (2H, m), 3.37 (1H, m), 3.64 (2H, m), 4.03 (1H, m), 5.23 (2H, m), 7.3 –7.7 (4H, m), 8.03 (2H, m), 8.19 (1H, m), 8.42 (1H, m).

REFERENCE EXAMPLE 12

IR$_{max}$ cm$^{-1}$ (neat): 3400, 1684, 1653, 1421, 1396, 1337, 1104;

NMR δ (CDCl$_3$): 1.82 (1H, m), 2.3–2.4 (3H, m), 2.5–3.25 (3H, m), 2.9–3.0 (3H, m), 3.45 (2H, m), 3.5–4.1 (5H, m), 4.13 (2H, m), 4.73 (1H, m), 5.23 (2H, m), 7.1–7.7 (4H, m), 8.20 (2H, m), 8.52 (1H, m).

REFERENCE EXAMPLE 13

IR$_{max}$ cm$^{-1}$ (neat): 3300, 1675, 1595, 1510, 1415, 1392, 1333, 1284, 1247, 1198, 1160, 1103;

NMR δ (CDCl$_3$): 2.33 (3H, s), 2.35 (1H, m), 2.51 (3H, s), 2,78 (2H, m), 3.34 (1H, dd, J=11.2 & 6.3 Hz), 3.50 (2H, m), 3.95 (1H, m), 4.10 (1H, dd, J=8.6 & 6.9Hz), 4.31 (1H, dd, J=8.6 & 5.6 Hz), 5.17 (1H, d, J=13.5 Hz), 5.24 (1H, d, J=13.5 Hz), 6.72 (1H, br. s), 7.09 (1H, d, J=7.9 Hz), 7.3–7.7 (3H, m), 8,22 (2H, d, J=8.2 Hz), 8.31 (1H, s).

REFERENCE EXAMPLE 14

IR$_{max}$ cm$^{-1}$ (KBr): 3320, 1705, 1656, 1518, 1399, 1340, 1160, 1115;

NMR δ (CDCl$_3$): 1.65 (1H, m), 2.33 (3H, s),2.50 (1H, s), 2.57 (3H, s), 2.83 (2H, m), 3.34 (1H, dd, J=10.8 & 5.9 Hz), 3.50 (2H, m), 3.97 (1H, m), 4.10 (1H, dd, J=11.2 & 6.9 Hz), 4.34 (1H, dd, J=7.9 & 6.3 Hz), 5.20 (2H, m), 7.06 (1H, dd, J=3.9 & 7.6 Hz), 7.42 (1H, m), 7.50 (2H, m), 8.22 (2H, d, J=8.6 Hz), 8.37 (1H, d, J=3.9 Hz).

REFERENCE EXAMPLE 15

IR$_{max}$ cm$^{-1}$ (KBr): 3320, 1700, 1665, 1605, 1550, 1518, 1428, 1402, 1342, 1178, 1118;

NMR δ (CDCl$_3$): 1.15–1.95 (7H, m), 2.24 (3H,s), 2.33 (3H, s), 2.4–2.7 (1H, m), 2.7 –3.0 (2H, m), 3.0–3.3 (2H, m), 3.3–3.5 (1H, m), 3.9–4.5 (4H, m), 5.24 (2H, s), 6.65 (1H, br. s), 7.51 (2H, d, J=8.4 Hz), 8.23 (2H, d, J=8.4 Hz).

REFERENCE EXAMPLE 16

IR$_{max}$ cm$^{-1}$ (KBr): 3290, 1707, 1687, 1645, 1522, 1421, 1340;

NMR δ (CDCl$_3$): 1.1–1.6 (5H, m), 1.6–2.0 (5H, m), 2.24 (3H, s), 2.33 (3H, s), 2.4 –2.6 (1H, m), 2.82 (2H, d, J=11.0 Hz), 3.2–3.6 (3H, m), 3.9–4.25 (2H, m), 4.3–4.5 (1H, m), 5.26 (2H, s), 6.51 (1H, br. s), 7.51 (2H, d, J=8.3 Hz), 8.24 (2H, d, J=8.3 Hz).

REFERENCE EXAMPLE 17

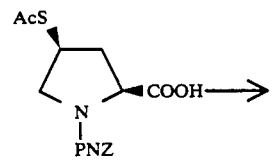

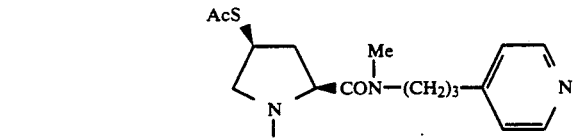

To a solution of cis-1-(p-nitrobenzyloxycarbonyl)-4-acetylthio-L-proline (736 mg; 2.0 mmol) in dry methylene chloride (6 ml), a catalytic amount of dimethylformamide was added, and a solution of oxalic chloride (305 mg; 2.4 mmol) in dry methylene chloride (2 ml) was added thereto. The resultant mixture was stirred at room temperature for 1 hour. Under ice-cooling, methyl [3-(4-pyridyl)propyl]amine (300 mg; 2.0 mmol) and a solution of triethylamine (485 mg; 4.8 mmol) in dry methylene chloride (2. ml) were added thereto, followed by stirring for 15 minutes. The reaction mixture was combined with aqueous sodium hydrogen carbonate solution, and the organic phase was separated from the aqueous phase, washed with aqueous sodium chloride solution and dried over anhydrous magnesium sulfate. After removal of the solvent, the residue was purified by silica gel column chromatography to give (2S,4S)-1-(p-nitrobenzyloxycarbonyl) -2-[3-(4-pyridyl)-propyl]methylaminocarbonyl-4-acetylthiopyrrolidine.

IR$_{max}$ cm$^{-1}$ (neat): 1715 (sh), 1700, 1654, 1600, 1518, 1340, 1160, 1107;

NMR δ (CDCl$_3$): 1.7–2.2 (3H, m), 2.33 (3H, s), 2.4–2.9 (3H, m), 2.9–3.1 (3H, m), 3.3–3.7 (3H, m), 3.9–4.2 (2H, m), 4.5–4.8 (1H, m), 5.21 (2H, s), 6.9 –7.2 (2H, m), 7.3–7.6 (2H, m), 8.1–8.3 (2H, m), 8.4–8.6 (2H, m).

REFERENCE EXAMPLES 18 TO 26

In the same manner as in Reference Example 17, the thioacetates as shown in Table 7 were obtained from the corresponding amines. The physical properties of the compounds obtained follow the Table.

TABLE 7

[Structure: Pyrrolidine with AcS group at 4-position, $(CH_2)_k$—CO—Q at 2-position, and PNZ on N]

| Reference Example No. | $(CH_2)_k$—CO—Q |
|---|---|
| 18 | —CON(Me)—$(CH_2)_2$—(4-pyridyl) |
| 19 | —CON(Me)—$(CH_2)_2$—(3-pyridyl) |
| 20 | —CON(Me)—$(CH_2)_3$—(3-pyridyl) |
| 21 | —CON(Me)—$(CH_2)_4$—(3-pyridyl) |
| 22 | —CON(Me)—$(CH_2)_3$—(2-pyridyl) |
| 23 | —CON(piperidine)—$(CH_2)_2$—N(Me)—Me |
| 24 | —CON(piperazine)—$(CH_2)_2$—O—TBDMS |
| 25 | —CON(piperazine)—$(CH_2)_3$—OH |
| 26 | —CON(piperazine)—$(CH_2)_2$—O—Me |

Physical Properties

REFERENCE EXAMPLE 18

IR$_{max}$ cm$^{-1}$ (neat): 1715 (sh), 1700, 1687 (sh), 1602, 1520, 1340, 1162, 1107;

NMR δ (CDCl$_3$): 1.7–2.0 (1H, m), 2.34 (3H, s), 2.5–3.1 (6H, m), 3.3–3.85 (3H, m), 3.85–4.2 (2H, m), 4.5–4.8 (1H, m), 5.22 (2H, s), 7.0–7.25 (2H, m), 7.4–7.6 (2H, m), 8.1–8.3 (2H, m), 8.45–8.65 (2H, m).

REFERENCE EXAMPLE 19

IR$_{max}$ cm$^{-1}$ (neat): 1730 (sh), 1692 (sh), 1660, 1507, 1390, 1335, 1150, 1110;

NMR δ (CDCl$_3$): 1.6–1.9 (1H, m), 2.34 (3H, s), 2.5–3.1 (6H, m), 3.3–4.3 (5H, m), 4.5–4.8 (1H, m), 5.22 (2H, s), 7.2–7.4 (1H, m), 7.4–7.7 (3H, m), 8.22 (2H, d, J=8.9 Hz), 8.47 (2H, br. s).

REFERENCE EXAMPLE 20

IR$_{max}$ cm$^{-1}$ (neat): 2930, 1715 (sh), 1704, 1696 (sh), 1650, 1518, 1420, 1400, 1340, 1105;

NMR δ (CDCl$_3$): 1.7–2.2 (3H, m), 2.33 (3H, s), 2.4–2.85 (3H, m), 2.85–3.15 (3H, m), 3.3–3.6 (2H, m), 3.85–4.2 (2H, m), 4.45–4.8 (1H, m), 5.22 (2H, s), 7.1–7.3 (1H, m), 7.3–7.6 (3H, m), 8.05–8.3 (2H, m), 8.3–8.6 (2H, m).

REFERENCE EXAMPLE 21

IR$_{max}$ cm$^{-1}$ (neat): 2925, 1714 (sh) 1682, 1654, 1518, 1420, 1400, 1340, 1160, 1115;

NMR δ (CDCl$_3$): 1.8–2.15 (2H, m), 2.33 (3H, s), 2.4–2.8 (3H, m), 2.8–3.1 (3H, m), 3.2–3.6 (3H, m), 3.9–4.2 (3H, m), 4.69 (1H, m), 5.20 (2H, m), 7.1–7.6 (4H, m), 8.1–8.3 (2H, m), 8.3–8.6 (2H, m).

REFERENCE EXAMPLE 22

IR$_{max}$ cm$^{-1}$ (neat): 1720 (sh), 1705, 1650, 1515, 1430, 1400, 1340, 1110;

(CDCl$_3$): 1.7–2.3 (2H, m), 2.33 (3H, s), 2.5–3.2 (7H, m), 3.2–3.7 (3H, m), 3.8–4.3 (2H, m), 5.6–5.8 (1H, m), 5.21 (2H, s), 7.0–7.3 (2H, m), 7.4–7.7 (3H, m), 8.0–8.3 (2H, m), 8.5–8.7 (1H, m).

REFERENCE EXAMPLE 23

IR$_{max}$ cm$^1$ (neat) 2920, 1700 (sh), 1688, 1642, 1507, 1400, 1336, 1100;

NMR δ (CDCl$_3$): 0.8–2.0 (10H, m), 2.21 (6H, s), 2.33 (3H, s), 2.5 3.2 (3H, m), 3.3–5.0 (5H, m), 5.22 (2H, s), 7.51 (2H, d, J=8.5 Hz), 8.22 (2H, d, J=8.5 Hz).

REFERENCE EXAMPLE 24

IR$_{max}$ cm$^{-1}$ (neat): 1700, 1660, 1523, 1438, 1402, 1342, 1253, 1103;

NMR δ (CDCl$_3$): 0.05 (6H, s), 0.89 (9H, s , 1.88 (1H, m), 2.33 (3H, s), 2.50 (6H, m), 3.40 (2H, m), 3.55 (2H, m), 3.72 (1H, m), 3.75 (2H, m), 4.00 (1H, m), 4.13 (2H, m), 4.72 (1H, m), 5.05–5.40 (2H, m), 7.50 (2H, m), 8.23 (2H, m).

REFERENCE EXAMPLE 25

IR$_{max}$ cm$^{-1}$ (neat): 3450 (br), 1700, 1653, 1521, 1435, 1342, 1120;

NMR δ (CDCl$_3$): 1.80–2.00 (1H, m), 2.2–2.9 (8H, m), 2.34 (3H, s), 3.3–3.9 (8H, m), 3.9–4.2 (2H, m), 4.6–4.8 (1H, m), 5.0–5.4 (2H, m), 7.51 (2H, d, J=8.9 Hz), 8.22 (2H, d, J =8.9 Hz).

REFERENCE EXAMPLE 26

NMR δ (CDCl$_3$): 1.90 (1H, m), 2.34 (3H, s), 2.30–2.85 (7H, m), 3.34 (3H x 0.3, s), 3.35 (3H x 0.7, s), 3.40–3.78 (7H, m), 4.01 (1H, m), 4.14 (1H, m), 4.75 (1H, m), 5.07 (0.3H, d, J 13.9 Hz), 5.23 (2H x 0.7, s), 5.31 (0.3H, d, J=13.9 Hz), 7.50 (2H,m) 8.23 (2H, m).

REFERENCE EXAMPLE 27

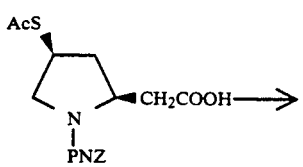

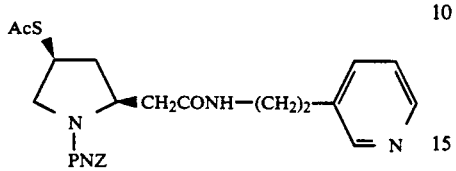

In the same manner as in Reference Example 1, there was obtained (2R,4S)-1-(p-nitrobenzyloxycarbonyl)-2-[2-(3-pyridylethyl) aminocarbonyl]methyl-4-acetylthiopyrrolidine from (*2R,4S)-1-(p-nitrobenzyloxycarbonyl)-2-carboxymethyl-4-acetylthiopyrrolidine (382 mg; 1.0 mmol).

IR$_{max}$ cm$^{-1}$ (neat): 3295 (br), 1690 (sh), 1680, 1650 (sh), 1513, 1418, 1395, 1338, 1100;

NMR δ (CDCl$_3$): 2.2–2.7 (2H, m) 2.34 (3H, s), 2.7–3.0 (3H, m), 3.25 (1H, dd, J=7.3 & 11.2 Hz), 3.4–3.7 (2H, m), 3.8–4.3 (3H, m), 5.19 (2H, s), 5.98 (1H, br.s), 7.15–7.35 (1H, m), 7.35–7.65 (3H, m), 8.22 (2H, d, J=8.6 Hz), 8.4–8.6 (2H, m).

REFERENCE EXAMPLES 28 AND 29

In the same manner as in Reference Example 27, the thioacetates as shown in Table 8 were obtained from the corresponding amines. The physical properties of the compounds obtained follow the Table.

TABLE 8

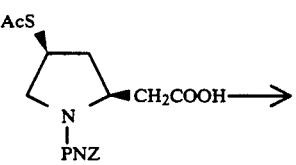

| Reference Example No. | (CH$_2$)$_k$—CO—Q |
|---|---|
| 28 | —CH$_2$CON(H)—CH$_2$—[piperidine]—N—Me |
| 29 | —CH$_2$CON(H)—(CH$_2$)$_2$—[piperidine]—N—Me |

Physical Properties

REFERENCE EXAMPLE 28

IR$_{max}$ cm$^{-1}$ (KBr): 3310, 1700, 1645, 1527, 1445, 1430, 1405, 1347, 1320, 1200, 1147, 1110;

NMR δ (CDCl$_3$): 1.15–1.55 (4H, m), 1.55–2.0 (5H, m), 2.25 (3H, s), 2.34 (3H, s), 2.4–2.7 (1H, m), 2.7–3.0 (3H, m), 3.0–3.6 (3H, m), 3.8–4.5 (3H, m), 5.21 (2H, s), 5.86 (1H, br. s), 7.52 (2H, d, J=8.8 Hz), 8.23 (2H, d, J=8.8 Hz).

REFERENCE EXAMPLE 29

IR$_{max}$ cm$^{-1}$ (KBr): 3290, 1690 (sh), 1687, 1630, 1520, 1424, 1342;

NMR δ (CDCl$_3$): 1.1–1 (5H, m), 1.5–1.8 (3H, m), 1.87 (2H, t, J=10.7 Hz), 2.25 (3H, s), 2.34 (3H, s), 2.4–2.7 (2H, m), 2.7–3.0 (3H, m), 3.1–3.4 (3H, m), 3.8–4.3 (3H, m), 5.21 (2H, s), 5.71 (1H, br. s), 7.51 (2H, d, J=8.6 Hz), 8.23 (2H, d, J=8.6 Hz).

REFERENCE EXAMPLE 30

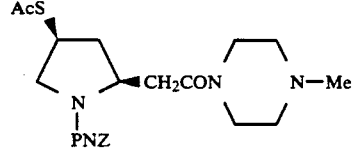

In the same manner as in Reference Example 2, there was obtained (2R,4S)-1-(p-nitrobenzyloxycarbonyl)-2-[(4-methyl) piperazin-1-yl]carbonylmethyl-4-acetylthiopyrrolidine from (2R,4S)-1-(p-nitrobenzyloxycarbonyl)-2-carboxymethyl-4-acetylthiopyrrolidine (382 mg; 1.0 mmol).

IR$_{max}$ cm$^{-1}$ (neat): 1687, 1634, 1515, 1420, 1398, 1340, 1285, 1100;

NMR δ (CDCl$_3$): 1.8–2.0 (1H, m), 2.2–2.6 (6H, m), 2.29 3H, s), 2.34 (3H, s), 2.6 2.9 (1H, m), 3.2–3.8 (5H, m), 3.8–4.0 (1H, m), 4.0 4.5 (2H, m), 5.21 (2H, s), 7.51 (2H, d, J=8.6 Hz), 8.23 (2H, d, J=8,6 Hz).

REFERENCE EXAMPLE 31

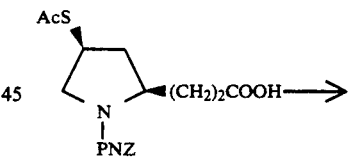

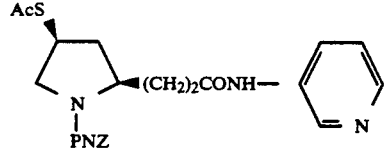

In the same manner as in Reference Example 2, there was obtained (2R,4S)-1-(p-nitrobenzyloxycarbonyl)-2-(3-pyridylamino)carbonylethyl -4-acetylthiopyrrolidine from (2R,4S)-1-(p-nitrobenzyloxycarbonyl)-2-(2-carboxy)ethyl-4-acetylthiopyrrolidine (198 mg; 0.50 mmol).

IR$_{max}$ cm$^{-1}$ (neat): 3280 (br), 1700 (sh), 1680, 1516, 1400, 1338;

NMR δ (CDCl$_3$): 1.6–2.8 (6H, m), 2.35 (3H, s), 3.28 (1H, dd, J=6.8 & 11.7 Hz), 3.92 (1H, m), 4.0–4.3 (2H, m), 5.26 (2H, s), 7.2 –7.4 (2H, m), 7.53 (2H, d, J =8.7 Hz), 8.25 (2H, d, J=8.7 Hz), 8.3–8.45 (1H, m), 8.67 (1H, d, J=2.3 Hz), 9.23 (1H, br. s).

REFERENCE EXAMPLE 32

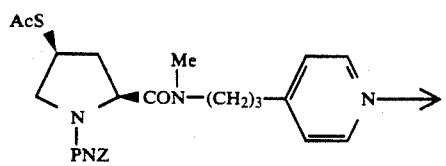
→
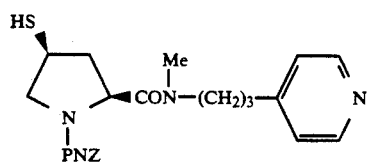

To a solution of (2S,4S)-1-(p-nitrobenzyloxycarbonyl) -2-(3-(4-pyridyl)propyl)methylaminocarbonyl)-4-acetylthiopyrrolidine (332 mg) in methanol (30 ml), 1N aqueous sodium hydroxide solution (0.70 ml) was added at room temperature, and the resultant mixture was stirred for 10 minutes. 1N Hydrochloric acid (0.70 ml) was added to the reaction mixture, and methanol was removed by distillation under reduced pressure. The residue was combined with dichloromethane, washed with water and dried over anhydrous magnesium sulfate, followed by removal of the solvent to give (2S,4S)-1-p-nitrobenzyloxycarbonyl-2-(3-(4-pyridyl)propyl) methylaminocarbonyl-4-mercaptopyrrolidine, which was subjected to the subsequent reaction without purification.

In the same manner as in Reference Example 32, the mercaptan compounds as shown in Table 9 were obtained from the corresponding thioacetates.

TABLE 9

| No. | k | Q |
|---|---|---|
| 1 | 0 | —NH—CH₂—(2-pyridyl) |
| 2 | 0 | —NH—(CH₂)₂—(2-pyridyl) |
| 3 | 0 | —N(Me)—(CH₂)₂—(2-pyridyl) |
| 4 | 0 | —N(Me)—(CH₂)₃—(2-pyridyl) |
| 5 | 0 | —NH—(3-pyridyl) |
| 6 | 0 | —NH—CH₂—(3-pyridyl) |
| 7 | 0 | —NH—(CH₂)₂—(3-pyridyl) |
| 8 | 0 | —NH—(CH₂)₃—(3-pyridyl) |
| 9 | 0 | —NH—(CH₂)₄—(3-pyridyl) |
| 10 | 0 | —N(Me)—(CH₂)₂—(3-pyridyl) |
| 11 | 0 | —N(Me)—(CH₂)₃—(3-pyridyl) |
| 12 | 0 | —N(Me)—(CH₂)₄—(3-pyridyl) |
| 13 | 0 | —NH—(4-pyridyl) |
| 14 | 0 | —NH—CH₂—(4-pyridyl) |
| 15 | 0 | —NH—(CH₂)₃—(4-pyridyl) |
| 16 | 0 | —N(Me)—(CH₂)₂—(4-pyridyl) |
| 17 | 0 | —NH—(CH₂)₂—(5-Me-2-pyridyl) |

TABLE 9-continued

[Structure: HS-pyrrolidine with PNZ on N, and (CH₂)ₖ—CO—Q substituent]

| No. | k | Q |
|---|---|---|
| 18 | 0 | —NH—(CH₂)₂—(3-methylpyridin-2-yl) |
| 19 | 0 | —N[(CH₂)₂—OH][CH₂—(3-pyridyl)] |
| 20 | 1 | —NH—(CH₂)₂—(3-pyridyl) |
| 21 | 2 | —NH—(3-pyridyl) |
| 22 | 0 | —N(piperazinyl)N—Me |
| 23 | 1 | —N(piperazinyl)N—Me |
| 24 | 0 | —NH—(CH₂)₂—(4-(N-Me)piperidinyl) |
| 25 | 1 | —NH—(CH₂)₂—(4-(N-Me)piperidinyl) |
| 26 | 0 | —N(piperidin-4-yl)(CH₂)₂—NMe₂ |
| 27 | 0 | —N(piperazinyl)N—(CH₂)₂—O—TBDMS |
| 28 | 0 | —NH—CH₂—(4-(N-Me)piperidinyl) |
| 29 | 1 | —NH—CH₂—(4-(N-Me)piperidinyl) |
| 30 | 0 | —N(piperazinyl)N—(CH₂)₂—OH |
| 31 | 0 | —N(piperazinyl)N—(CH₂)₂—OMe |

REFERENCE EXAMPLE 33

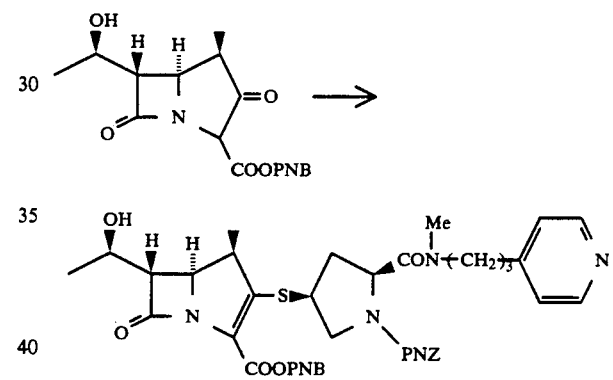

To a solution of (4R,5R,6S,8R)-p-nitrobenzyl-4-methyl-6-(1-hydroxyethyl)-1-azabicyclo[3.2.0]hept-3,7-dione-2-carboxylate (218 mg) in dry acetonitrile (2.0 ml), diisopropylethylamine (94 mg) and diphenyl chlorophosphate (178 mg) were added under ice-cooling, and the resultant mixture was stirred at the same temperature for 2 hours. A solution of (2S,4S)-p-nitrobenzyloxycarbonyl-2-(3-(4-pyridyl) propyl)methylaminocarbonyl-4-mercaptopyrrolidine (311 mg) and diisopropylethylamine (94 mg) in dry acetonitrile (3.0 ml) was added to the reaction mixture, followed by stirring for 2 hours. The reaction mixture was diluted with ethyl acetate, washed with aqueous potassium phosphate solution and a saturated aqueous sodium chloride solution in order and dried over anhydrous magnesium sulfate. After removal of the solvent, the residue was purified by silica gel column chromatography to give (4R,5S,6S,8R,2'S,4'S)-p-nitrobenzyl -3-[1-p-nitrobenzyloxycarbonyl-2-((3-(4-pyridyl)propyl) methylaminocarbonyl)pyrrolidin-4-ylthio]-4-methyl-6-(1-hydroxyethyl)-1-azabicyclo[3.2.0]hept-2-en-7-one-2-carboxylate.

IR$_{max}$ cm$^{-1}$ (neat): 3380, 1763, 1700, 1644, 1601, 1517, 1403, 1339;

NMR δ (CDCl₃): 1.28 (3H, d, J=6.9 Hz), 1.37 (3H, d, J 6.3 Hz), 3.08, 2.96 (3H as a whole, each s), 5.21 (2H, br.s), 5.24 (1H, d, J=13.8 Hz), 5.51 (1H, d, J=13.8 Hz), 6.97–7.20 (2H, m), 7.35–7.63 (2H, m), 7.65 (2H, d, J 8.9 Hz), 8.10 8.30 (4H, m), 8.52 (2H, m).

REFERENCE EXAMPLE 34

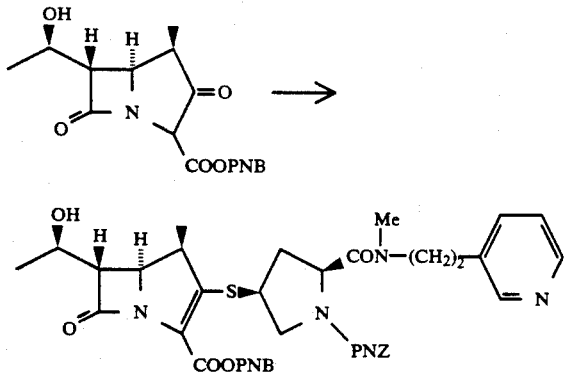

To a solution of (4R,5R,6S,8R)-p-nitrobenzyl-4-methyl -6-(1-hydroxyethyl)-1-azabicyclo[3.2.0]hept-3,7-dione-2-carboxylate (54 mg) in dry acetonitrile (1.0 ml), diisopropylethylamine (22 mg) and diphenyl chlorophosphate (45 mg) were added under ice-cooling, and the resultant mixture was stirred at the same temperature for 1 hour. A solution of (2S,4S)-1-p-nitrobenzyloxycarbonyl-2-(2-(3-pyridyl)ethyl) methylaminocarbonyl-4-mercaptopyrrolidine (95 mg) and diisopropylethylamine (22 mg) in dry acetonitrile (1.0 ml) was added to the reaction mixture, followed by stirring for 1.5 hours. The reaction mixture was diluted with dichloromethane, washed with water and dried over anhydrous magnesium sulfate. After removal of the solvent, the residue was purified by silica gel column chromatography to give (4R,5S,6S,8R,2'S,4'S)-p-nitrobenzyl-3-[1-p-nitrobenzyloxycarbonyl -2-((2-(3-pyridyl)ethyl)methylaminocarbonyl)pyrrolidin-4-ylthio]-4-methyl-6-(1-hydroxyethyl)-1-azabicyclo [3.2.0]hept-2-en-7-one-2-carboxylate.

IR$_{max}$ cm$^{-1}$ (neat): 3400, 1755, 1690, 1512, 1332;

NMR δ (CDCl$_3$): 1.27 (3H, d, J=7.0 Hz), 1.37 (3H, d, J=6.3 Hz), 2.88, 2.96, 3.00 (3H as a whole, each s), 3.27 (1H, m), 5.30 (3H, m), 5.50 (1H, d, J=13.5 Hz), 7.26 (1H, m), 7.4–7.6 (3H, m), 7.65 (2H, d, J=8.6 Hz), 8.22 (4H, d, J=8.6 Hz), 8.4–8.6 (2H, m).

REFERENCE EXAMPLE 35

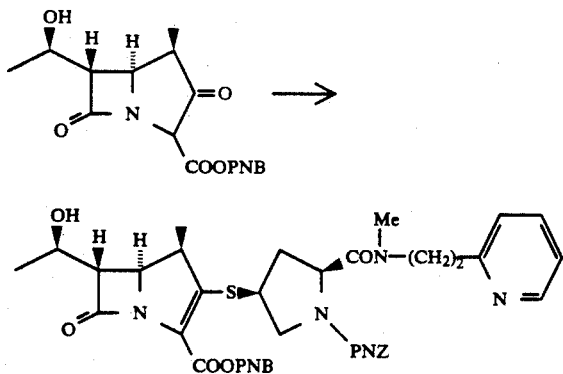

To a solution of (4R,5R,6S,8R)-p-nitrobenzyl-4-methyl -6-(1-hydroxyethyl)-1-azabicyclo[3.2.0]hept-3,7-dione-2-carboxylate (181 mg) in dry acetonitrile (2.0 ml), diisopropylethylamine (81 mg) and diphenyl chlorophosphate (175 mg) were added under ice-cooling, and the resultant mixture was stirred at the same temperature for 1 hour. A solution of (2S,4S)-p-nitrobenzyloxycarbonyl-2-(2-(2-pyridyl)ethyl)methylaminocarbonyl -4-mercaptopyrrolidine (303 mg) in dry acetonitrile (3.0 ml) and then diisopropylethylamine (81 mg) were added to the reaction mixture, followed by stirring for 2 hours. The reaction mixture was diluted with ethyl acetate, washed with aqueous potassium phosphate solution and a saturated aqueous sodium chloride solution in order and dried over magnesium sulfate. After removal of the solvent, the residue was purified by silica gel column chromatography to give (4R,5S,6S,8R,2'S,4'S)-p-nitrobenzyl-3 -3-[1-p-nitrobenzyloxycarbonyl-2-((2-(2-pyridyl)ethyl)methylaminocarbonyl) pyrrolidin-4-ylthio]-4-methyl-6-(1-hydroxyethyl) -1-azabicyclo[3.2.0]hept-2-en-7-one-2-carboxylate.

NMR δ (CDCl$_3$): 1.28 (3H, d, J=7.3 Hz), 1.34 (3H, d, J=6.3 Hz), 1.87 (1H, m), 2.73 (1H, m), 2.92, 2.93, 2.95, 3.01 (3H as a whole, each s), 4.80 (1H, m), 5.26 (3H, m), 5.49 (1H, d, J=13.9 Hz), 7.00–7.75 (7H, m), 8.22 (4H, m), 8.50 (1H, m).

REFERENCE EXAMPLE 36

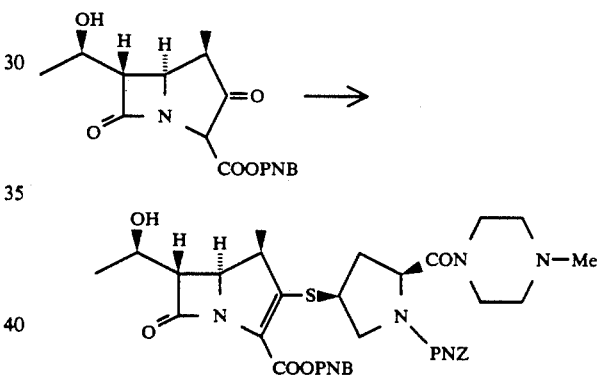

To a solution of (4R,5R,6S,8R)-1-p-nitrobenzyl-4-methyl -6-(1-hydroxyethyl)-1-azabicyclo[3.2.0]hept-3,7-dione-2-carboxylate (2.55 g) in dry acetonitrile (10.0 ml), diisopropylethylamine (1.09 g) and diphenyl chlorophosphate (2.06 g) were added under ice-cooling, and the resultant mixture was stirred at the same temperature for 2 hours. A solution of (2S,4S)-p-nitrobenzyloxycarbonyl-2-(4-methylpiperazin-1-ylcarbonyl) -4-mercaptopyrrolidine (3.08 g) and diisopropylethylamine (1.09 g) in dry acetonitrile (10.0 ml) was added to the reaction mixture, followed by stirring for 4 hours. The reaction mixture was diluted with ethyl acetate, washed with aqueous potassium phosphate solution and a saturated aqueous sodium chloride solution in order and dried over anhydrous magnesium sulfate. After removal of the solvent, the residue was purified by silica gel column chromatography to give (4R,5S,6S,8R,2'S,4'S)-p-nitrobenzyl-3-[1-p-nitrobenzyloxycarbonyl -2-(4-methylpiperazin-1-ylcarbonyl)pyrrolidin -4-ylthio]-4-methyl-6-(1-hydroxyethyl)-1-azabicyclo [3.2.0]hept-2-en-7-one-2-carboxylate.

IR$_{max}$ cm$^{-1}$ (neat): 3400, 1750, 1695, 1630, 1593, 1500, 1423, 1390, 1324, 1271, 1193, 1120;

NMR δ (CDCl$_3$): 1.26 (3H, d, J=7.3 Hz), 1.34 (3H, d, J=6.3 Hz), 1.91 (1H, m), 2.32 (3H, s), 2.73 (1H, s), 4.72

(1H, m), 5.22 (3H, m), 5.43 (1H, d, J=13.9 Hz), 7.40-7.60 (2H, m), 7.64 (2H, d, J=.8.9 Hz), 8.20 (4H, d, J =8.9 Hz).

REFERENCE EXAMPLES 37 to 50

In the same manner as in Reference Example 36, the compounds as shown in Table 10 were obtained. The physical properties of the compounds obtained follow the Table.

TABLE 10

[Structure: penem-like core with OH, isopropyl, COOPNB, S-linked pyrrolidine bearing (CH$_2$)$_k$-CO-Q and N-PNZ]

| Reference Example No. | k | Q |
|---|---|---|
| 37 | 0 | -NH-CH$_2$-(2-pyridyl) |
| 38 | 0 | -N(Me)-(CH$_2$)$_3$-(2-pyridyl) |
| 39 | 0 | -NH-(3-pyridyl) |
| 40 | 0 | -NH-(4-pyridyl) |
| 41 | 0 | -N(Me)-(CH$_2$)$_2$-(4-pyridyl) |
| 42 | 0 | -N((CH$_2$)$_2$-OH)(CH$_2$-(3-pyridyl)) |
| 43 | 0 | -NH-CH$_2$-(3-pyridyl) |
| 44 | 0 | -N(Me)-(CH$_2$)$_3$-(3-pyridyl) |
| 45 | 0 | -N(Me)-(CH$_2$)$_4$-(3-pyridyl) |

TABLE 10-continued

[Same core structure]

| Reference Example No. | k | Q |
|---|---|---|
| 46 | 1 | -NH-(CH$_2$)$_2$-(3-pyridyl) |
| 47 | 2 | -NH-(3-pyridyl) |
| 48 | 1 | -N(piperazinyl)-N-Me |
| 49 | 0 | -N(piperazinyl)-N-(CH$_2$)$_3$-OH |
| 50 | 0 | -N(piperazinyl)-N-(CH$_2$)$_2$-O-Me |

Physical Properties

REFERENCE EXAMPLE 37

IR$_{max}$ cm$^{-1}$ (neat): 3370, 1763, 1700, 1602, 1517, 1430, 1398, 1341, 1203, 1130, 1106;

NMR δ (CDCl$_3$): 1.27 (3H, d, J=7.3 Hz), 1.36 (3H, d, J=6.3 Hz), 2.80 (1H, m), 3.28 (1H, dd, J=3.0 & 6.9 Hz), 3.36 (1H, m), 3.50 (1H, dd, J=8.0 & 10.9 Hz), 3.71 (1H, m), 4.30 (2H, m), 5.10 5.50 (4H, m), 7.10-7.70 (6H, m), 7.98 (1H, m), 8.21 (4H, d, J=8.9 Hz), 8.39 (1H, m).

REFERENCE EXAMPLE 38

IR$_{max}$ cm$^{-1}$ (neat): 3400, 1761, 1697, 1637, 1515, 1426, 1400, 1340, 1202, 1175, 1132, 1104;

NMR δ (CDCl$_3$): 1.28 (3H, d, J=6.9 Hz), 1.34 (3H, d, J=5.6 Hz), 1.88 (3H, m), 2.50 -2.90 (4H, m), 2.92, 2.97, 3.00, 3.11 (3H as a whole, each s), 3.28 (1H, m), 3.48 (4H, m), 3.69 (1H, m), 3.87 (1H, m), 4.27 (3H, m), 4.75 (1H, m), 5.23 (3H, m), 5.48 (1H, d, J=13.9 Hz), 7.39 (1H, dd, J=4.9 & 8.9 Hz), 7.50 (1H, d, J=8.9 Hz), 8.06 (1H, t, J=8.9 Hz), 8.18 (4H, d, J=8.9 Hz), 8.48 (1H, m).

REFERENCE EXAMPLE 39

IR$_{max}$ cm$^{-1}$ (neat): 3330, 1761, 1710, 1603, 1519, 1420, 1340, 1205;

NMR δ (CDCl$_3$): 1.26 (3H, d, J=7.3 Hz , 1.35 (3H, d, J=6.3 Hz), 3.35 (2H, m), 3.84 (1H, m), 4.03 (1H, m), 4.28 (2H, m), 4.56 (1H, m), 5.17 (1H, d, J=13.6 Hz), 5.30 (2H, s), 5.33 (1H, d, J=13.6 Hz), 7.60 (2H, d, J=8.9 Hz), 8.16 (4H, d, J=8.9 Hz), 8.35 (1H, m), 8.58 (1H, s).

REFERENCE EXAMPLE 40

IR$_{max}$ cm$^{-1}$ (neat): 3290, 1760, 1702, 1586, 1508, 1397, 1337, 1203,1183;

NMR δ (CDCl$_3$): 1.27 (3H, d, J=7.2 Hz), 1.35 (3H, d, J=6.3 Hz), 2.30 (1H, m), 2.64 (1H, m), 3.32 (2H, m), 3.53 (1H, m), 3.83 (1H, m), 4.00 (1H, m), 4.28 (2H, m), 4.55 (1H, m), 5.18 (1H, d, J=13.8 Hz), 5.25 (2H, m), 5.38 (1H, d, J 13.8 Hz), 7.47 (2H, m), 7.60 (2H, d, J=8.6 Hz), 8.17 (2H, d, J=8.6 Hz), 8.45 (2H, m).

REFERENCE EXAMPLE 41

IR$_{max}$ cm$^{-1}$ (neat): 3400, 1762, 1698, 1643, 1600, 1517, 1339;

NMR δ (CDCl$_3$): 1.27 (3H, d, J=6.9 Hz), 1.37 (3H, d, J 6.3 Hz), 2.89, 2.96, 2.98 (3H as a whole, each s), 5.22 (2H, br. s), 5.25 (1H, d, J=13.9 Hz), 5.49 (1H d, J=13.9 Hz), 7.00-7.23 (2H, m), 7.40-7.58 (2H, m), 7.65 (2H, d, J=8.6 Hz), 8.21 (4H, m), 8.53 (2H, m).

REFERENCE EXAMPLE 42

IR$_{max}$ cm$^{-1}$ (neat): 3380, 1755, 1693, 1643, 1508, 1337;

NMR δ (CDCl$_3$): 1.27 (3H, d, J=7.3 Hz), 1.36 (3H, d, J=6.3 Hz), 2.03 (1H, m), 2.67 (1H, m), 3.20-3.95 (9H, m), 4.05 (1H, m), 4.26 (2H, m), 4.96 (1H, d, J 13.5 Hz), 5.23 (4H, m), 5.48 (1H, d, J=13.5 Hz), 7.26 (1H, m), 7.51 (2H, d, J=8.9 Hz), 7.65 (3H, d, J=8.6 Hz), 8.22 (4H, m), 8.53 (2H, m).

REFERENCE EXAMPLE 43

IR$_{max}$ cm$^{-1}$ (KBr): 3350, 1774, 1704, 1656, 1600, 1508, 1423, 1395, 1337, 1315;

NMR δ (CDCl$_3$): 1.24 (3H, m), 1.33 (3H, d, J=6.3 Hz), 2.47 (1H, m), 2.91 (1H, m), 3.31 (2H, m), 3.54 (1H, dd, J=5.3 & 11.2 Hz), 3.79 (1H, m), 4.02 (1H, dd, J=6.0 & 11.2 Hz), 4.20-4.60 (5H, m), 5.12 (1H, d, J=14.2 Hz), 5.20 (2H, br. s), 5.40 (1H, d, J=14.2 Hz), 7.22 (1H, m), 7.50 (2H, m), 7.60 (2H, d, J 8.9 Hz), 7.62(1H, m), 8.13 (4H, d, J=8.9 Hz), 8.45 (1H, m), 8.50(1H, s).

REFERENCE EXAMPLE 44

IR$_{max}$ cm$^{-1}$ (KBr): 3410, 1768, 1704, 1653, 1603, 1522, 1422, 1403, 1342, 1262;

NMR δ (CDCl$_3$): 1.28 (3H, m), 1.37 (3H d, J=6.3 Hz), 1.87 (2H, m), 2.70 (3H, m), 2.97, 2.98, 3.09 (3H as a whole, each s), 3.30-3.80 (7H, m), 4.78 (2H, m), 5.24 (1H, d, J=13.8 Hz), 5.30 (2H, br. s), 5.46 (2H, d, J=13.8 Hz), 7.22 (1H, m), 7.40 (1H, m), 7.50 (2H, d, J=8.6 Hz), 7.65 (2H, d, J=8.9 Hz), 8.2 (4H, m), 8.45 (2H, m).

REFERENCE EXAMPLE 45

IR$_{max}$ cm$^{-1}$ (KBr): 3300, 1773, 1707, 1663, 1604, 1518, 1438, 1402, 1340, 1280, 1265, 1206, 1168, 1147, 1109;

NMR δ (CDCl$_3$): 1.27 (3H, m), 1.37 (3H, d, J=6.3 Hz), 1.80-2.10 (4H, m), 2.67 (2H, m), 2.88, 2.93, 2.95, 3.04 (3H as a whole, each s), 5.20 (2H, br.s), 5.25 (1H, d, J=13.5 Hz), 5.48 (1H, d, J=13.5 Hz), 7.23 (1H, m), 7.40 (1H, m), 7.51 (2H, d, J=8.9 Hz), 7.65 (2H, d, J=8.3 Hz), 8.12 (4H, d, J=8.9 Hz), 8.42 (2H, m).

REFERENCE EXAMPLE 46

IR$_{max}$ cm$^{-1}$ (neat): 3350, 1760, 1696, 1652, 1517, 1419, 1400, 1338, 1196, 1130, 1102;

NMR δ (CDCl$_3$): 1.28 (3H, d, J=7.3 Hz , 1.37 (3H, d, J=6.0 Hz), 2,82 (2H, m), 5.20 (2H, br. s), 5.23 (1H, d, J=14.0 Hz), 5.50 (1H, d, J 14.0 Hz), 7.25 (1H, m), 7.55 (3H, m), 7.66 (2H, d, J=8.9 Hz), 8.23 (4H, d, J =8.9 Hz), 8.44 (1H, br.s), 8.48 (1H, d, J=5.0 Hz).

REFERENCE EXAMPLE 47

IR$_{max}$ cm$^{-1}$ (neat): 3350, 1760, 1700, 1684, 1598, 1518, 1400, 1336;

NMR δ (CDCl$_3$): 1.27 (3H, d, J=6.9 Hz), 1.37 (3H, d, J 6.3 Hz), 2.20-2.80 (5H, m), 3.20-3.50 (2H, m), 3.28 (1H, dd, J=2.6 & 6.9 Hz), 3.50-3.80 (1H, m), 4.00-4.35 (5H, m), 5.37 (2H, ABq, J=76.9 & 13.9 Hz), 7.53 (2H, d, J=8.9 Hz), 7.65 (2H, d, J =8.9 Hz), 8.10-8.50 (7H, m), 8.64 (1H, s), 9.09 (1H, br.s).

REFERENCE EXAMPLE 48

IR$_{max}$ cm$^{-1}$ (neat): 3370, 1760, 1695, 1627, 1517, 1433, 1420, 1398, 1337, 1194, 1132, 1101;

NMR δ (CDCl$_3$): 1.28 (3H, d, J=7.3 Hz), 1.37 (3H, d, J=6.3 Hz), 2.30 (3H, s), 5.25 (3H,m), 5.50 (1H, d, J=13.9 Hz), 7.51 (2H, d, J=8.9 Hz), 7.65 (2H, d, J=8.9Hz), 8.22 (4H, m).

REFERENCE EXAMPLE 49

IR$_{max}$ cm$^{-1}$ (neat) 3200 (br), 1760, 1700, 1652, 1512, 1336;

NMR δ (CDCl$_3$) 1.28 (3H, m), 1.36 (3H, d, J=6.3 Hz), 2.02 (3H, m), 2.73 (1H, m), 3.10 (2H, m), 3.24-4.80 (18H, m), 5.05-5.56 (4H, m), 7.43 (2H x 0.3, d, J=7.9 Hz), 7.51 (2H x 0.7, d, J=8.9 Hz). 7.64 (2H, d, J =8.6 Hz), 8.20 (4H, m).

REFERENCE EXAMPLE 50

IR$_{max}$ cm$^{-1}$ (neat): 3420 (br), 1763, 1700, 1648, 1602, 1520, 1438, 1243;

NMR δ (CDCl$_3$): 1.26 (3H, m), 1.35 (3H, d, J=6.3 Hz), 2.92 (1H, m), 2.30-2.85 (7H, m), 3.34 (3H x 0.5, s), 3.56 (3H x 0.5, s), 3.20-3.83 (9H, m), 4.20 (2H, m), 4.76 (1H, m), 5.08-5.55 (4H, m), 7.44 (2H x 0.5, d, J=8.9 Hz), 7.52 (2H x 0.5, d, J 8.6 Hz), 7.65 (2H, d, J=8.9 Hz), 8.20 (4H, m).

REFERENCE EXAMPLE 51

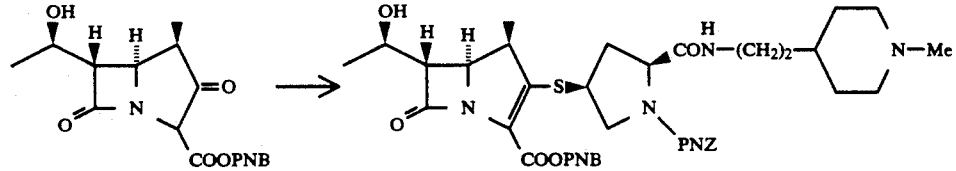

To a solution of (4R, 5R,6S,8R)-p-nitrobenzyl-4-methyl-6-(1-hydroxyethyl) -1-azabicyclo[3.2.0]hept-3,7-dione-2-carboxylate (217 mg) in dry acetonitrile (2.0 ml), diisopropylethylamine (93 mg) and diphenyl chlorophosphate (178 mg) were added under ice-cooling, and the resultant mixture was stirred for 3 hours. A solution of (2S,4S)-p-nitrobenzyloxycarbonyl -2-(2-(1-methylpiperizin-4-yl)ethyl)aminocarbonyl-4-mercaptopyrrolidine (293 mg) and 1,8-diazabicyclo [5.4.0]-7- undecene (218 mg) in a mixture of dry acetonitrile (2.0 ml) and dry tetrahydrofuran (4.0 ml) was added to the reaction mixture, followed by stirring for 1 hour. The reaction mixture was combined with a phosphate buffer (pH, 7.0) and extracted with dichloromethane 3 times. The organic layer was dried over anhydrous magnesium sulfate. After removal of the solvent, the residue was purified by silica gel column chromatography to give (4R,5S,6S,8R,2'S,4'S)-p-nitrobenzyl-3-[1-p-naitrobenzyloxycarbonyl -2-((2-(1-methylpiperizin-4-yl)ethyl)aminocarbonyl)-pyrrolidin-4-ylthio] -4-methyl-6-(1-hydroxyethyl)-1-azabicyclo [3.2.0]hept-2-en-7-one-2-carboxylate.

IR$_{max}$ cm$^{-1}$ (neat): 3300, 1762, 1703, 1519, 1487, 1342, 1204;

NMR δ (CDCl$_3$): 1.24 (3H, d, J=7.3 Hz), 1.36 (3H, d, J=6.3 Hz), 2.35 (3H, br.s).

REFERENCE EXAMPLE 52

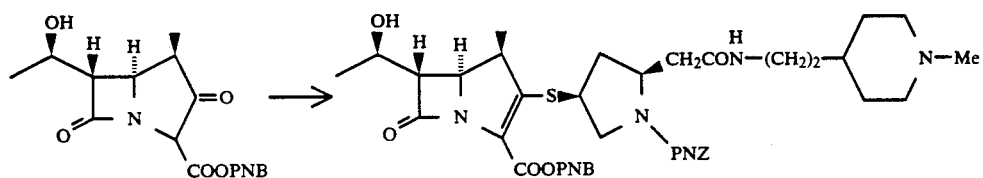

In the same manner as in Reference Example 51, there was obtained (4R,5S,6S,8R,2'S,4'S)-p-nitrobenzyl-[1-p-nitrobenzyloxycarbonyl -2-((2-(1-methylpiperidin-4-yl) ethyl)aminocarbonylmethyl)pyrrolidin-4-ylthio]-4-methyl-6-(1-hydroxyethyl) -1-azabicyclo[3.2.0]hept-2-en-7-one-2-carboxylate.

IR$_{max}$ cm$^{-1}$ (neat): 3350, 1758, 1693, 1518, 1339;
NMR δ (CDCl$_3$): 1.25 (3H, d, J=7.0 Hz), 1.36 (3H, d, J=6.3 Hz), 2.35 (3H, br.s).

REFERENCE EXAMPLE 53

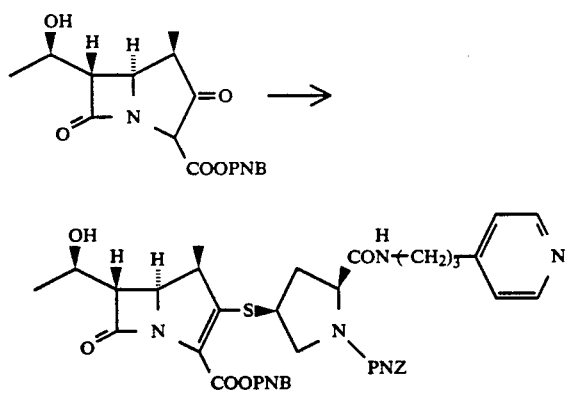

To a solution of (4R,5R,6S,8R)-p-nitrobenzyl-4-methyl -6-(1-hydroxyethyl)-1-azabicyclo[3.2.0]hept-3,7-dione-2-carboxylate (256 mg) in dry acetonitrile (1.5 ml), diisopropylethylamine (108 mg) and diphenyl chlorophosphate (206 mg) were added under ice-cooling, and the resultant mixture was stirred at the same temperature for 4 hours. To a suspension of (2S,4S)-1-p-nitrobenzyloxycarbonyl-2-(3-(4-pyridyl) propyl-)aminocarbonyl-4-mercaptopyrrolidine (450 mg) in dry acetonitrile (3.0 ml), bis(trimethylsilyl)acetamide (165 mg) was added, and the mixture was heated to 60° C., followed by allowing to stand. The thus obtained solution was added to the above phosphate solution under cooling with ice, and diisopropylethylamine (108 mg) was added thereto. After 15 minutes, 1,8-diazabicyclo[5.4.0]-7-undecene (203 mg) was added, followed by stirring for 1 hour. The reaction mixture was diluted with ethyl acetate, washed with aqueous potassium phosphate solution and a saturated aqueous sodium chloride solution in order and dried over anhydrous magnesium sulfate. After removal of the solvent, the residue was dissolved in ethyl acetate (50 ml), 0.1 N hydrochloric acid (5.0 ml) was added while cooling with ice, and the resultant mixture was stirred vigorously. A phosphate buffer (pH, 7.0) was added to the reaction mixture, which was extracted with dichloromethane three times. The extracts were combined together, dried over anhydrous magnesium sultate, concentrated and purified by silica gel column chromatography to give (4R,5S,6S,8R,2'S,4'S)-p-nitrobenzyl -3-[1-p-nitrobenzyloxycarbonyl-2-((3-(4-pyridyl)-propyl) aminocarbonyl)pyrrolidin-4-ylthio]-4-methyl-6-(1-hydroxyethyl) -1-azabicyclo[3.2.0]hept-2-en-7-one-2-carboxylate.

IR$_{max}$ cm$^{-1}$ (neat): 3350, 1760, 1697, 1518, 1340;
NMR δ (CDCl$_3$): 1.26 (3H, d, J=7.0 Hz), 1.36 (3H, d, J=6.3 Hz), 1.84 (2H, m), 2.60 (2H, m), 7.09 (2H, m), 7.49 (2H, m), 7.62 (2H, m), 8.20 (4H, m), 8.48 (2H, d, J=5.9 Hz).

REFERENCE EXAMPLES 54 TO 60

In the same manner as in Reference Example 53, the compounds as shown in Table 11 were obtained. The physical properties of the compounds obtained follow the Table.

TABLE 11

| Reference Example No. | k | Q |
|---|---|---|
| 54 | 0 | —N(H)—(CH$_2$)$_2$—(2-pyridyl) |
| 55 | 0 | —N(H)—(CH$_2$)$_2$—(3-pyridyl) |
| 56 | 0 | —N(H)—(CH$_2$)$_3$—(4-pyridyl) |

TABLE 11-continued

Structure:

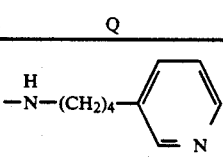

| Reference Example No. | k | Q |
|---|---|---|
| 57 | 0 | −NH−(CH₂)₄−(3-pyridyl) |
| 58 | 0 | −NH−CH₂−(4-pyridyl) |
| 59 | 0 | −NH−(CH₂)₂−(5-methyl-2-pyridyl) |
| 60 | 0 | −NH−(CH₂)₂−(3-methyl-2-pyridyl) |

Physical Properties

REFERENCE EXAMPLE 54

NMR δ (CDCl₃): 1.26 (3H, d, J=7.3 Hz), 1.36 (3H, d, J=6.3 Hz), 5.11 (1H, d, J=13.5 Hz), 5.18 (2H, m ), 5.42 (1H, d, J=13.5 Hz), 7.00-7.80 (6H, m), 8.05 (1H, m), 8.19 (4H, d, J=8.9 Hz), 8.39 (1H, m).

REFERENCE EXAMPLE 55

IR$_{max}$ cm$^{-1}$ (neat): 3400, 1742, 1680, 1500, 1309, 1251;

NMR δ (CDCl₃): 1.27 (3H, d, J=6.9 Hz), 1.36 (3H, d, J=6.3 Hz), 1.95 (1H, m), 2.51 (1H, m), 2.84 (2H, m), 3.32 (2H, m), 3.49 (3H, m), 3.73 (1H, m), 3.97 (1H, m), 5.20 (3H, m), 5.42 (1H, d, J=13.5 Hz), 7.23 (1H, m), 7.51 (3H, m), 7.62 (2H, d, J=8.6 Hz), 8.18 (4H, d, J=8.6 Hz), 8.43 (2H, m).

REFERENCE EXAMPLE 56

IR$_{max}$ cm$^{-1}$ (neat): 3225, 1770, 1703, 1655, 1518, 1422, 1399, 1342, 1318, 1273, 1203, 1166, 1137, 1105;

NMR δ (CDCl₃): 1.24 (3H, d, J=7.3 Hz), 1.35 (3H, d, J=6.3 Hz), 1.82 (3H, m), 2.61 (2H, m), 3.36 (4H, m), 3.50 (1H, m), 3,76 (1H, m), 4.08 (1H, m), 4.28 (2H, m), 4.38 (1H, m), 5.14 (1H, d, J=13.9 Hz), 5.24 (2H, br. s), 5.40 (1H, d, J=13.9 Hz), 7.20 (1H, t, J 6.0 Hz), 7.48 (3H, br.s), 7.62 (2H, d, J 8.6 Hz), 8.18 (4H, d, J=8.3 Hz), 8.42 (2H, br. s).

REFERENCE EXAMPLE 57

IR$_{max}$ cm$^{-1}$ (neat): 3400, 1767, 1703, 1647, 1520, 1422, 1403, 1343, 1262;

NMR δ (CDCl₃): 1.26 (3H, d, J=7.3 Hz), 1.37 (3H, d, J=6.0 Hz), 2.16 (1H, m), 2.60 (3H, m), 3.27 (5H, m), 3.47 (1H, m), 3.73 (1H, m), 4.02 (1H, m), 4.32 (3H, m), 5.23 (3H, m), 5.46 (1H, d, J=13.9 Hz), 7.22 (1H, m), 7.46 (3H, m), 7.64 (2H, d, J=8.9 Hz), 8.21 (4H, d, J=8.9 Hz), 8.42 (2H, m).

REFERENCE EXAMPLE 58

NMR δ0 (CDCl₃): 1.27 (3H, d, J=7.3 Hz), 1.36 (3H, d, J=6.3 Hz), 3.29 (1H, dd, J=3.0 & 5.9Hz), 5.17 (1H, d, J=12.9 Hz), 5.23 (2H, br.s), 5.42 (1H, d, J=12.9 Hz), 7.18 (2H, m), 7.48 (2H, m), 7.63 (2H, d, J=8.9 Hz), 8.22 (4H, m), 8.51 (2H, m).

REFERENCE EXAMPLE 59

IR$_{max}$ cm$^{-1}$ (neat): 3370, 1756, 1682, 1597, 1510, 1420, 1392, 1335, 1196, 1103;

NMR δ (CDCl₃): d, J=7.3 Hz), 1.34 (3H, d, J=6.3 Hz), 2.49 (3H, s), 2.78 (2H, m), 3.29 (1H, dd, J=2.3 & 6.6 Hz), 3.34 (1H, m), 3.49 (2H, m), 3.74 (1H, m), 4.00 (1H, m), 4.27 (2H, m), 4.36 (1H, m), 5.17 (1H, d, J=13.9 Hz), 5.19 (2H, s), 5.42 (1H, d, J 13.9 Hz), 7.07 (1H, d, J=7.9 Hz), 7.44 (3H, m), 7.60 (2H, d, J=8.9 Hz), 8.16 (4H, d, J=8.9 Hz), 8.28 (1H, s).

REFERENCE EXAMPLE 60

IR$_{max}$ cm$^{-1}$ (neat): 3400, 1767, 1703, 1521, 1441, 1399, 1343, 1262, 1203;

NMR δ (CDCl₃): 1.24 (3H, d, J=7.3 Hz), 1.37 (3H, d, J=6.3 Hz), 2.56 (3H, s), 2.84 (2H, m), 3.20-3.65 (6H, m), 3.73 (1H, m), 4.08 (1H, m), 4.20-4.45 (4H, m), 5.20 (1H, d, J=13.5 Hz), 5.19 (2H, br. s), 5.45 (1H, d, J=13.5 Hz), 7.04 (1H, dd, J=4.9 & 7.6 Hz). 7,43 (1H, d, J=7.6 Hz), 7.50 (2H, m), 7.63 (2H, d, J=8.6 Hz), 8.21 (4H, d, J=8.6 Hz), 8.35 (1H, d, J=4.9 Hz).

REFERENCE EXAMPLE 61

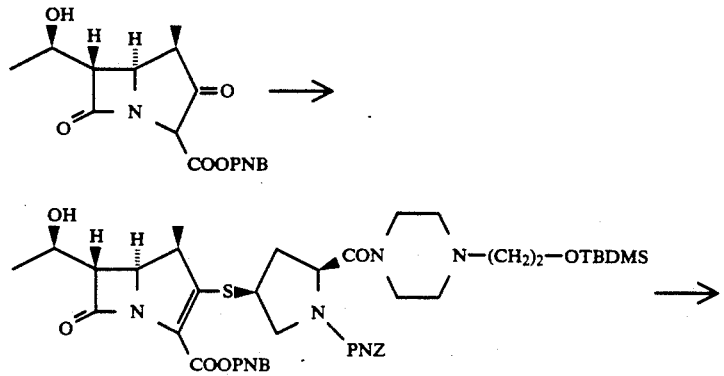

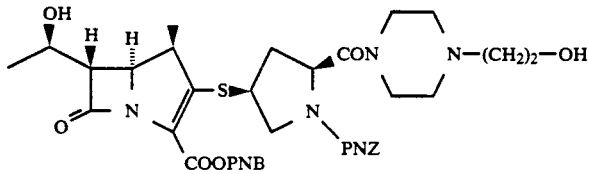

a) To a solution of (4R,5R,6S,8R)-p-nitrobenzyl-4-methyl-6-(1-hydroxyethyl) -1-azabicyclo[3.2.0]hept-3,7-dione-2-carboxylate (256 mg) in dry acetonitrile (2.0 ml), diisopropylethylamine (108 mg) and diphenyl chlorophosphate (200 mg) were added under ice-cooling, and the resultant mixture was stirred at the same temperature for 2 hours. A solution of 1-p-nitrobenzyloxycarbonyl-2-(4-(2-(t-butyldimethylsilyloxy) ethyl)piperazin-2-ylcarbonyl)-4-mercaptopyrrolidine (491 mg) and diisopropylethylamine (108 mg) in dry acetonitrile (2.0 ml) was added thereto, followed by stirring for 2 hours. The reaction mixture was diluted with ethyl acetate, washed with aqueous potassium phosphate solution and a saturated aqueous sodium chloride solution in order and dried over anhydrous magnesium sulfate. After removal of the solvent, the residue was purified by silica gel column chromatography to give (4R,5S,6S,8R,2'S,4'S)-p-nitrobenzyl -3-[1-p-nitrobenzyloxycarbonyl-2-(4-(2-(t-butyldimethylsilyloxy) ethyl)piperazin-1-ylcarbonyl)pyrrolidin-4-ylthio]-4-methyl-6-(1-hydroxyethyl)-1-azabicyclo[3.2.0]-hept -2-en-7-one-2-carboxylate.

IR$_{max}$ cm$^{-1}$ (neat): 3250, 1763, 1703, 1664, 1657, 1521, 1342;

NMR δ (CDCl$_3$): 0.06 (6H, s), 0.89 (9H, s), 1.29 (3H, d, J=7.3 Hz), 1.37 (3H, d, J=6.3 Hz), 2.50 (6H, m), 3.38 (2H, m), 3.56 (2H, m), 3.76 (2H, m), 5.10–5.55 (4H, m), 7.40–7.60 (2H, m), 7.65 (2H, d, J=8.3 Hz), 8.24 (4H, m).

b) The thus obtained (4R,5S,6S,8R,2'S,4'S)-p-nitrobenzyl -3-[1-p-nitrobenzyloxycarbonyl-2-(4-(2-(t-butyldimethylsilyloxy) ethyl)piperazin-1-ylcarbonyl)pyrrolidin-4-ylthio]-4-methyl-6-(1-hydroxyethyl)-1-azabicyclo[3.2.0]hept-2-en-7-one-2-carboxylate (476 mg) was dissolved in dry tetrahydrofuran (4.0 ml) and stirred at room temperature. Acetic acid (657 mg) and a 1 N tetrahydrofuran solution of tetrabutylammonium fluoride (2.16 ml) were added, and the resultant mixture was stirred at the same temperature for 9 hour. A phosphate buffer (pH, 7.0) was added to the reaction mixture, which was extracted with dichloromethane three times. The organic layer was dried over anhydrous magnesium sulfate, followed by removal of the solvent. The residue was purified by silica gel column chromatography to give (4R,5S,6S,8R,2'S,4'S)-p-nitrobenzyl-3-[1-p-nitrobenzyloxycarbonyl -2-(4-(2-hydroxyethyl)piperazin-1-ylcarbonyl)pyrrolidin -4-ylthio]-4-methyl-6-(1-hydroxyethyl)-1-azabicyclo [3.2.0]hept-2-en-7-one-2-carboxylate.

IR$_{max}$ cm$^{-1}$ (neat): 3250, 1762, 1703, 1658, 1521, 1342;

NMR δ (CDCl$_3$): 1.28 (3H, d, J=7.3 Hz), 1.36 (3H, d, J=6.0 Hz), 1.92 (1H, m), 2.80 (6H, m), 2.93 (1H, m), 3.20–3.80 (9H, m), 4.08 (1H, m), 4.26 (3H, m), 4.73 (1H, m), 5.25 (3H, m), 5.49 (1H, d, J=13.8 Hz), 7.35–7.60 (2H, m), 7.64 (2H, d, J=8.9 Hz), 8.22 (4H, m).

REFERENCE EXAMPLE 62

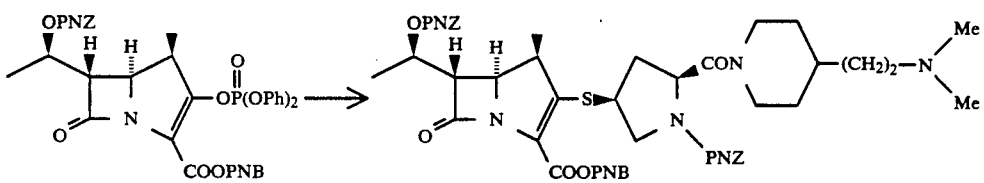

To a solution of (4R,5R,6S,8R)-p-nitrobenzyl-3-(diphenylphosphoryloxy) -4-methyl-6-(1-(p-nitrobenzyloxycarbonyloxy) ethyl)-1-azabicyclo[3.2.0]hept-2-en-7-one-2-carboxylate (714 mg) in dry acetonitrile (3.0 ml), a solution of (2S,4S)-1-p-nitrobenzyloxycarbonyl-2-(4-(2-dimethylaminoethyl) piperidin-1-ylcarbonyl)-4-mercaptopyrrolidine (505 mg) in dry acetonitrile (3.0 ml) was added under ice-cooling, and 1,8-diazabicyclo[5.4.0]-7-undecene (182 mg) was added thereto, followed by stirring at the same temperature for 2 hours. The reaction mixture was diluted with dichloromethane, washed with a saturated aqueous sodium chloride solution and dried over anhydrous magnesium sulfate. After removal of the solvent, the residue was purified by silica gel column chromatography to give (4R,5S,6S,8R,2'S,4'S)-p-niatrobenzyloxycarbonyl-3-[1-p-nitrobenzyl -2-(4-(2-dimethylaminoethyl)piperidin-1-ylcarbonyl)pyrrolidin-4-ylthio]-4-methyl-6-(1-(p-nitrobenzyloxycarbonyloxy)ethyl) -1-azabicyclo[3.2.0-]hept-2-en-7-one-2-carboxylate.

NMR δ (CDCl$_3$): 1.22 (3H, d, J=7.3 Hz), 1.29 (3H, d, J=6.3 Hz), 2.38 (6H, s), 5.00–5.50 (6H, m), 7.00–7.70 (6H, m), 8.18 (6H, m).

What is claimed is:

1. A compound of the formula:

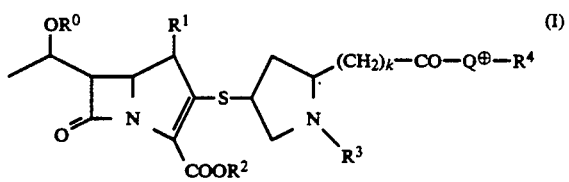

wherein $R^0$ is a hydrogen atom or a protective group for hydroxyl, $R^1$ is a lower alkyl group, $R^2$ is a protective group for carboxyl or a negative charge, $R^3$ is a hydrogen atom or a protective group for amino, $R^4$ is a lower alkyl group or a substituted lower alkyl group, k is an integer of 0 to 4, and $Q^\oplus$ is a quaternary nitrogen atom-containing group represented by either one of the formulas (1) to (4):

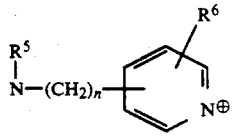
(1)

wherein $R^5$ is a hydrogen atom, a lower alkyl group or a 2-hydroxyethyl group, $R^6$ is a hydrogen atom or a lower alkyl group and n is an integer of 0 to 4;

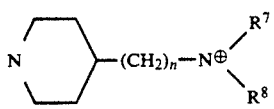
(2)

wherein $R^7$ and $R^8$ are each a lower alkyl group or may be combined together to form a lower alkylene group, or $R^8$ represents a substituted lower alkyl group and n is as defined above;

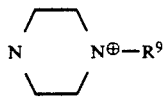
(3)

wherein $R^9$ is a lower alkyl group or a substituted lower alkyl group; or

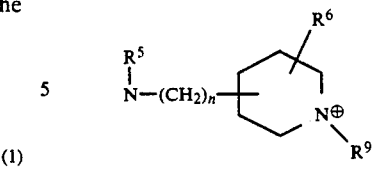
(4)

wherein $R^5$, $R^6$, $R^9$ and n are each as defined above, and when $R^2$ is said protective group, said compound contains an acid residue or its salt.

2. The compound according to claim 1, wherein $R^0$ and $R^3$ are each a hydrogen atom, $R^2$ is a negative charge or its salt.

3. The compound according to claim 2, wherein $Q^\oplus$ is a quaternary nitrogen atom-containing group represented by either one of the formulas (1) or (3).

4. The compound according to claim 3, wherein $Q^\oplus$ is a quaternary nitrogen atom-containing group represented by the formula (1) wherein $R^5$ is a hydrogen atom or a methyl group, $R^6$ is a hydrogen atom and n is an integer of 0 to 4.

5. The compound according to claim 3, wherein $Q^\oplus$ is a quaternary nitrogen atom-containing group represented by the formula (3) wherein $R^9$ is a methyl group.

6. The compound according to claim 1, wherein $R^4$ is a $C_1$-$C_5$ alkyl group, a $C_2$-$C_5$ alkanoyl($C_1$-$C_5$)alkyl group, a carbamoyl($C_1$-$C_5$)alkyl group, a $C_1$-$C_5$ alkylaminocarbonyl-($C_1$-$C_5$) alkyl group, a di($C_1$-$C_5$)alkylaminocarbonyl($C_1$-$C_5$)-alkyl group or a hydroxy($C_2$-$C_5$)alkyl group.

7. The compound according to claim 1, wherein $R^1$ is a methyl group.

8. The compound according to claim 1, wherein k is zero.

9. The compound according to claim 1, which has a (5S)-configuration.

10. The compound according to claim 1, which has a (4R,5S,6S,8R)-configuration.

11. A pharmaceutical composition which comprises as an active ingredient a pharmaceutically effective amount of at least one of the compounds as claimed in any of claims 1, 2, 3, 4, 5, 6, 7, 8, 9 or 10, and at least one pharmaceutically acceptable inert carrier or diluent.

* * * * *